(12) United States Patent
Levchik et al.

(10) Patent No.: US 8,927,015 B2
(45) Date of Patent: Jan. 6, 2015

(54) FORMULATIONS FOR DELIVERING INSULIN

(75) Inventors: Halina Levchik, Tarrytown, NY (US); Moses O. Oyewumi, Yorktown Heights, NY (US); Shingai Majuru, Brewster, NY (US); William Elliott Bay, Ridgefield, CT (US); Jun Liao, Yorktown Heights, NY (US); Puchun Liu, Chappaqua, NY (US); Steven Dinh, Briarcliff Manor, NY (US); Nikhil Dhoot, Dombivli (IN)

(73) Assignee: Emisphere Technologies, Inc., Roseland, NJ (US)

( * ) Notice: Subject to any disclaimer, the term of this patent is extended or adjusted under 35 U.S.C. 154(b) by 472 days.

(21) Appl. No.: 12/297,147

(22) PCT Filed: Apr. 12, 2007

(86) PCT No.: PCT/US2007/066560
§ 371 (c)(1),
(2), (4) Date: Oct. 14, 2008

(87) PCT Pub. No.: WO2007/121318
PCT Pub. Date: Oct. 25, 2007

(65) Prior Publication Data
US 2010/0151009 A1 Jun. 17, 2010

Related U.S. Application Data

(60) Provisional application No. 60/791,842, filed on Apr. 12, 2006, provisional application No. 60/857,747, filed on Nov. 7, 2006.

(51) Int. Cl.
| | | |
|---|---|---|
| A61K 38/28 | (2006.01) | |
| A61K 9/20 | (2006.01) | |
| A61K 47/02 | (2006.01) | |
| A61K 47/42 | (2006.01) | |
| A61K 9/14 | (2006.01) | |

(52) U.S. Cl.
CPC ............. *A61K 38/28* (2013.01); *A61K 9/2013* (2013.01); *A61K 9/2009* (2013.01); *A61K 9/145* (2013.01); *A61K 9/2077* (2013.01); *A61K 9/2027* (2013.01); *A61K 9/2095* (2013.01); *A61K 9/2063* (2013.01)
USPC ............................ 424/465; 514/5.9; 514/774

(58) Field of Classification Search
CPC .... A61K 9/2009; A61K 9/2063; A61K 38/28
USPC ..................................... 424/465; 514/5.9, 774
See application file for complete search history.

(56) References Cited

U.S. PATENT DOCUMENTS

| | | |
|---|---|---|
| 4,043,996 A | 8/1977 | Donnelly et al. |
| 4,064,008 A | 12/1977 | Petersen et al. |
| 4,176,117 A | 11/1979 | Oudem et al. |
| 4,232,425 A | 11/1980 | Wojcik |
| 4,374,063 A | 2/1983 | Consolazio et al. |
| 4,402,873 A | 9/1983 | Vollmer et al. |
| 4,421,685 A | 12/1983 | Chance et al. |
| 4,427,583 A | 1/1984 | England et al. |
| 4,889,920 A | 12/1989 | Muller et al. |
| 5,093,474 A | 3/1992 | Grossman et al. |
| 5,135,866 A | 8/1992 | Heifetz et al. |
| 5,210,182 A | 5/1993 | Nasrallah et al. |
| 5,288,408 A | 2/1994 | Schmidt et al. |
| 5,401,516 A | 3/1995 | Milstein et al. |
| 5,443,841 A | 8/1995 | Milstein et al. |
| 5,447,728 A | 9/1995 | Milstein et al. |
| 5,451,410 A | 9/1995 | Milstein et al. |
| 5,459,241 A | 10/1995 | Moy et al. |
| 5,461,031 A | 10/1995 | De Felippis |
| 5,474,978 A | 12/1995 | Bakaysa et al. |
| 5,504,188 A | 4/1996 | Baker et al. |
| 5,540,939 A | 7/1996 | Milstein et al. |
| 5,541,155 A | 7/1996 | Leone-Bay et al. |
| 5,547,929 A | 8/1996 | Anderson, Jr. et al. |
| 5,578,323 A | 11/1996 | Milstein et al. |
| 5,601,846 A | 2/1997 | Milstein et al. |
| 5,629,020 A | 5/1997 | Leone-Bay et al. |
| 5,643,957 A | 7/1997 | Leone-Bay et al. |
| 5,646,242 A | 7/1997 | Baker et al. |
| 5,650,386 A | 7/1997 | Leone-Bay et al. |
| 5,650,486 A | 7/1997 | De Felippis |
| 5,667,806 A | 9/1997 | Kantor |
| 5,693,338 A | 12/1997 | Milstein |
| 5,693,609 A | 12/1997 | Baker et al. |
| 5,709,861 A | 1/1998 | Santiago et al. |

(Continued)

FOREIGN PATENT DOCUMENTS

| | | |
|---|---|---|
| WO | WO-94/05258 | 3/1994 |
| WO | WO-94/23767 A1 | 10/1994 |

(Continued)

OTHER PUBLICATIONS

Constantino et al. (Biochimica et Biophysica Acta, 1253(1), Published Nov. 15, 1995, p. 69-74).*
Foss et al. (European Journal of Pharmaceutics and Biopharmaceutics, vol. 57, Issue 2, pp. 163-169, Published in 2004).*
Lowman et al. (Journal of Pharmaceutical Sciences, vol. 88, No. 9, Published Sep. 1999, pp. 933-937).*
U.S. Appl. No. 60/718,829, filed Sep. 19, 2005.
U.S. Appl. No. 60/576,088, filed Jun. 1, 2004.
U.S. Appl. No. 60/576,397, filed Jun. 1, 2004.
U.S. Appl. No. 60/576,105, filed Jun. 1, 2004.
U.S. Appl. No. 60/571,090, filed May 14, 2004.

(Continued)

Primary Examiner — Richard Schnizer
Assistant Examiner — Alma Pipic
(74) Attorney, Agent, or Firm — Blank Rome LLP

(57) ABSTRACT

Oral insulin formulations and processes for preparing oral insulin formulations are provided.

1 Claim, 20 Drawing Sheets

(56) References Cited

U.S. PATENT DOCUMENTS

| | | |
|---|---|---|
| 5,714,167 A | 2/1998 | Milstein et al. |
| 5,747,642 A | 5/1998 | De Felippis |
| 5,750,147 A | 5/1998 | Kantor |
| 5,766,633 A | 6/1998 | Milstein et al. |
| 5,773,647 A | 6/1998 | Leone-Bay et al. |
| 5,776,888 A | 7/1998 | Leone-Bay et al. |
| 5,792,451 A | 8/1998 | Sarubbi et al. |
| 5,804,688 A | 9/1998 | Leone-Bay et al. |
| 5,811,127 A | 9/1998 | Milstein et al. |
| 5,820,881 A | 10/1998 | Milstein |
| 5,824,345 A | 10/1998 | Milstein |
| 5,840,340 A | 11/1998 | Milstein et al. |
| 5,863,944 A | 1/1999 | Leone-Bay et al. |
| 5,866,536 A | 2/1999 | Leone-Bay et al. |
| 5,873,358 A | 2/1999 | Gonda et al. |
| 5,876,710 A | 3/1999 | Leone-Bay et al. |
| 5,879,681 A | 3/1999 | Leone-Bay et al. |
| 5,888,477 A | 3/1999 | Gonda et al. |
| 5,922,675 A | 7/1999 | Baker et al. |
| 5,935,601 A | 8/1999 | Leone-Bay et al. |
| 5,939,381 A | 8/1999 | Leone-Bay et al. |
| 5,952,297 A | 9/1999 | De Felippis et al. |
| 5,955,503 A | 9/1999 | Leone-Bay et al. |
| 5,958,451 A | 9/1999 | Chen |
| 5,962,710 A | 10/1999 | Gschneidner et al. |
| 5,965,121 A | 10/1999 | Leone-Bay et al. |
| 5,970,973 A | 10/1999 | Gonda et al. |
| 5,972,387 A | 10/1999 | Milstein et al. |
| 5,976,569 A | 11/1999 | Milstein |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,034,054 A | 3/2000 | DeFelippis et al. |
| 6,051,258 A | 4/2000 | Kantor |
| 6,051,551 A | 4/2000 | Hughes et al. |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,084,112 A | 7/2000 | Ho et al. |
| 6,090,915 A | 7/2000 | Herreid |
| 6,090,958 A | 7/2000 | Leone-Bay et al. |
| 6,099,856 A | 8/2000 | Milstein et al. |
| 6,100,285 A | 8/2000 | Kantor |
| 6,100,298 A | 8/2000 | Leone-Bay et al. |
| 6,180,140 B1 | 1/2001 | Leone-Bay et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,268,335 B1 | 7/2001 | Brader |
| 6,313,088 B1 | 11/2001 | Leone-Bay et al. |
| 6,331,318 B1 | 12/2001 | Milstein |
| 6,335,316 B1 | 1/2002 | Hughes et al. |
| 6,344,213 B1 | 2/2002 | Leone-Bay et al. |
| 6,358,504 B1 | 3/2002 | Leone-Bay et al. |
| 6,362,009 B1 * | 3/2002 | Munoz et al. ............. 506/30 |
| 6,375,981 B1 | 4/2002 | Gilleland et al. |
| 6,375,983 B1 | 4/2002 | Kantor et al. |
| 6,384,278 B1 | 5/2002 | Tang et al. |
| 6,391,303 B1 | 5/2002 | Haas et al. |
| 6,395,774 B1 | 5/2002 | Milstein |
| 6,399,798 B2 | 6/2002 | Gschneidner et al. |
| 6,413,550 B1 | 7/2002 | Milstein et al. |
| 6,428,780 B2 | 8/2002 | Leone-Bay et al. |
| 6,440,480 B2 | 8/2002 | Dorp et al. |
| 6,440,929 B1 | 8/2002 | Milstein et al. |
| 6,444,641 B1 | 9/2002 | Flora |
| 6,461,545 B1 | 10/2002 | Kantor |
| 6,461,643 B2 | 10/2002 | Milstein et al. |
| 6,465,426 B2 | 10/2002 | Brader |
| RE37,971 E | 1/2003 | Baker et al. |
| 6,525,020 B2 | 2/2003 | Leone-Bay et al. |
| 6,531,448 B1 | 3/2003 | Brader |
| 6,534,288 B1 | 3/2003 | Habermann et al. |
| 6,551,992 B1 | 4/2003 | DeFelippis et al. |
| 6,558,706 B2 | 5/2003 | Kantor et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,630,348 B1 | 10/2003 | Lee et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,663,898 B2 | 12/2003 | Milstein |
| 6,693,073 B2 | 2/2004 | Milstein et al. |
| 6,693,208 B2 | 2/2004 | Gscheidner et al. |
| 6,693,898 B1 | 2/2004 | Su et al. |
| 6,699,467 B2 | 3/2004 | Leone-Bay et al. |
| 6,777,207 B2 | 8/2004 | Kjeldsen et al. |
| 6,852,694 B2 | 2/2005 | Van Antwerp et al. |
| 6,906,028 B2 | 6/2005 | DeFelippis et al. |
| 6,960,561 B2 | 11/2005 | Boderke et al. |
| 2001/0003001 A1 | 6/2001 | Leone-Bay et al. |
| 2001/0039258 A1 | 11/2001 | Milstein et al. |
| 2002/0001591 A1 | 1/2002 | Santiago et al. |
| 2002/0013497 A1 | 1/2002 | Gschneidner et al. |
| 2002/0028250 A1 | 3/2002 | Milstein |
| 2002/0040061 A1 | 4/2002 | Tang et al. |
| 2002/0052422 A1 | 5/2002 | Milstein et al. |
| 2002/0065255 A1 | 5/2002 | Bay et al. |
| 2002/0102286 A1 | 8/2002 | Kantor et al. |
| 2002/0119910 A1 | 8/2002 | Leone-Bay et al. |
| 2002/0120009 A1 | 8/2002 | Leone-Bay et al. |
| 2002/0127202 A1 | 9/2002 | Leone-Bay et al. |
| 2002/0155993 A1 | 10/2002 | Milstein |
| 2003/0008900 A1 | 1/2003 | Leone-Bay et al. |
| 2003/0012817 A1 | 1/2003 | Milstein et al. |
| 2003/0045579 A1 | 3/2003 | Leone-Bay et al. |
| 2003/0072740 A1 | 4/2003 | Milstein et al. |
| 2003/0078302 A1 | 4/2003 | Leone-Bay et al. |
| 2003/0133953 A1 | 7/2003 | Milstein et al. |
| 2003/0198658 A1 | 10/2003 | Milstein |
| 2003/0198666 A1 * | 10/2003 | Abbas et al. ............. 424/452 |
| 2003/0225300 A1 | 12/2003 | Leone-Bay et al. |
| 2003/0232085 A1 | 12/2003 | Milstein et al. |
| 2003/0235612 A1 | 12/2003 | Leone-Bay et al. |
| 2004/0022856 A1 | 2/2004 | Sarubbi et al. |
| 2004/0062773 A1 | 4/2004 | Santiago et al. |
| 2004/0068013 A1 | 4/2004 | Leone-Bay et al. |
| 2004/0106825 A1 | 6/2004 | Bay et al. |
| 2004/0110839 A1 | 6/2004 | Leone-Bay et al. |

FOREIGN PATENT DOCUMENTS

| | | |
|---|---|---|
| WO | WO-95/11690 A1 | 5/1995 |
| WO | WO-95/28838 A1 | 11/1995 |
| WO | WO-95/28920 A1 | 11/1995 |
| WO | WO-96/09813 | 4/1996 |
| WO | WO-96/10396 | 4/1996 |
| WO | WO-96/12473 A1 | 5/1996 |
| WO | WO-96/12474 A1 | 5/1996 |
| WO | WO-96/12475 | 5/1996 |
| WO | WO-96/21464 A1 | 7/1996 |
| WO | WO-96/30036 | 10/1996 |
| WO | WO-96/33699 | 10/1996 |
| WO | WO-96/40070 | 12/1996 |
| WO | WO-96/40076 | 12/1996 |
| WO | WO-9639835 | 12/1996 |
| WO | WO-97/10197 A1 | 3/1997 |
| WO | WO-97/31938 | 9/1997 |
| WO | WO-97/36480 A1 | 10/1997 |
| WO | WO-97/47288 | 12/1997 |
| WO | WO-98/21951 A1 | 5/1998 |
| WO | WO-98/25589 A1 | 6/1998 |
| WO | WO-98/34632 A1 | 8/1998 |
| WO | WO-98/49135 | 11/1998 |
| WO | WO-98/50341 A1 | 11/1998 |
| WO | WO-99/16427 A1 | 4/1999 |
| WO | WO-00/06184 A1 | 2/2000 |
| WO | WO-00/06534 A1 | 2/2000 |
| WO | WO-00/07979 A1 | 2/2000 |
| WO | WO-00/40203 A1 | 7/2000 |
| WO | WO-00/46182 A1 | 8/2000 |
| WO | WO-00/47188 | 8/2000 |
| WO | WO-00/48589 | 8/2000 |

(56) References Cited

FOREIGN PATENT DOCUMENTS

| WO | WO-00/50386 A1 | 8/2000 |
| WO | WO-00/59480 A1 | 10/2000 |
| WO | WO-00/59863 | 10/2000 |
| WO | WO-01/32130 A1 | 5/2001 |
| WO | WO-01/32596 | 5/2001 |
| WO | WO-01/34114 | 5/2001 |
| WO | WO-01/44199 A1 | 6/2001 |
| WO | WO-01/51454 A1 | 7/2001 |
| WO | WO-01/70219 A1 | 9/2001 |
| WO | WO-01/92206 A1 | 12/2001 |
| WO | WO-02/02509 A1 | 1/2002 |
| WO | WO-02/15959 A1 | 2/2002 |
| WO | WO-02/16309 A1 | 2/2002 |
| WO | WO-02/19969 A1 | 3/2002 |
| WO | WO-02/20466 A1 | 3/2002 |
| WO | WO-02/064115 | 8/2002 |
| WO | WO-02/069937 A1 | 9/2002 |
| WO | WO-02/070438 | 9/2002 |
| WO | WO-02/100338 | 12/2002 |
| WO | WO-03/026582 | 4/2003 |
| WO | WO-03/045306 | 6/2003 |
| WO | WO-03/057170 | 7/2003 |
| WO | WO-03/057650 A1 | 7/2003 |
| WO | WO-2004/062587 | 7/2004 |
| WO | WO-2004/080401 | 9/2004 |
| WO | WO 2004/080401 A2 * | 9/2004 |
| WO | WO-2004/104018 | 12/2004 |
| WO | WO-2005/107462 | 11/2005 |
| WO | WO-2005/112633 | 12/2005 |
| WO | WO-2005/115406 | 12/2005 |
| WO | WO-2005/117854 | 12/2005 |
| WO | WO-2006/017541 | 2/2006 |
| WO | WO-2007/035718 | 3/2007 |

OTHER PUBLICATIONS

U.S. Appl. No. 60/571,092, filed May 14, 2004.
U.S. Appl. No. 60/571,195, filed May 14, 2004.
U.S. Appl. No. 60/571,194, filed May 14, 2004.
U.S. Appl. No. 60/571,093, filed May 14, 2004.
U.S. Appl. No. 60/571,055, filed May 14, 2004.
U.S. Appl. No. 60/571,151, filed May 14, 2004.
U.S. Appl. No. 60/571,315, filed May 14, 2004.
U.S. Appl. No. 60/571,144, filed May 14, 2004.
U.S. Appl. No. 60/571,089, filed May 14, 2004.

* cited by examiner

Profile of Insulin Dissolution Study- 4

Profile of Insulin Dissolution Study- 5

Co-lyophilized Insulin/4-CNAB(50 units insulin/80 mg 4-CNAB); Study 56B( Formulation Lot# 1206-29) Dose: 1 tablet NHP Serum Insulin Levels: Insulin/4-CNAB Colyophilized
(50 units/160 mg); ITR Study 66A; 1 tablet/NHP Insulin/4CNAB(50 units/160mg) Colyophilized Insulin/4-CNAB Co-lyophilized ( 50 units/240 mg); Blood Glucose Change: Study 60A; 1 tablet/HNP Serum Insulin levels: Co-lyophilized insulin 50 units/240 mg 4CNAB; study 60A Oral Insulin 90-Day Study Results (ITT)

Heterogeneity of Patient Population
(Difference between Screening and Baseline; Baseline HbA1c)

Analysis Methodology Based on Initial Stabilty and Baseline HbA1c

Effect of Initial Stability on change in HbA1c from Baseline to Day 90 or ET

Effect of Initial Stability on change in HbA1c from Baseline to Day 90 or ET

Change in HbAlc in Group 1 and Group 4
During Study Period

Number of Patients in Group 1 and Group 4 Reaching Target

Difference in Glycemic Parameters Between Group 1 and Group4

FORMULATIONS FOR DELIVERING INSULIN

CROSS REFERENCE TO PRIOR APPLICATIONS

This application is the U.S. national phase of International Application No. PCT/US07/66560, filed Apr. 12, 2007, which claims priority of Provisional Application No. 60/791,842 filed Apr. 12, 2006 and to Provisional Application No. 60/857,747 filed Nov. 7, 2006, the specifications of both of which are herein incorporated by reference. The International Application was published in English on Oct. 25, 2007 as WO 2007/121318 under PCT Article 21(2)

FIELD OF THE INVENTION

The present invention relates to pharmaceutical formulations (e.g. oral pharmaceutical formulations) containing insulin and one or more delivery agents, e.g. (4-CNAB or sodium 4-CNAB), and methods of treating subjects suffering from diabetes with such pharmaceutical formulations.

BACKGROUND OF THE INVENTION

There is a need for orally administered insulin that provides sufficient insulin bioavailability, and processes for preparing such pharmaceutical compositions.

SUMMARY OF THE INVENTION

Methods of synthesizing pharmaceutical formulations containing insulin and a delivery agent compound have an effect on the bioavailability of the insulin upon administration of the pharmaceutical formulation (e.g. upon oral administration by a human). The present invention provides processing techniques that facilitate the delivery of insulin upon administration with a delivery agent compound.

One embodiment of the present invention is a solid oral pharmaceutical composition comprising 4-CNAB, or a pharmaceutically acceptable salt thereof, recombinant human insulin, povidone, dibasic calcium phosphate, and magnesium stearate.

Another embodiment of the present invention is a process for preparing a solid oral pharmaceutical formulation by introducing insulin or an analog thereof to an aqueous solution that contains a delivery agent compound, drying the solution to obtain an insulin/delivery agent powder, optionally granulating the powder with intragranular excipients, optionally adding extragranular excipients to the powder or granules, and forming a unit dosage form from the resulting composition (e.g., compressing the composition into tablets or filling capsules with the composition).

Another embodiment of the present invention is a process for preparing a solid oral insulin pharmaceutical composition by (a) preparing a solution of a delivery agent and insulin or an analog thereof; (b) freeze-drying the insulin/delivery agent solution; (c) milling the insulin/delivery agent colyophilized powder obtained by freeze-drying the insulin/delivery agent solution; (d) mixing the milled co-lyophilized powder with intragranular excipients; (e) dry granulating the mixture formed in step (d), (f) adding extragranular excipients; and (g) forming a unit dosage form from the resulting composition (e.g., compressing the composition into tablets or filling capsules with the composition). Dry granulation may be performed, for example, by roller compaction or slugging and then milling the resulting product.

Another embodiment of the present invention is a process for preparing a solid oral insulin pharmaceutical composition by (a) preparing a solution of a delivery agent and insulin or an analog thereof; (b) performing rotary evaporation on the insulin/delivery agent solution; and (c) forming a unit dosage form from the product of step (b) (e.g., tableting the insulin/delivery agent powder or adding the insulin/delivery agent powder to capsules). This process may further include one or more of the steps of (d) milling the insulin/delivery agent powder obtained by rotary evaporation; (e) mixing the milled powder with intragranular excipients; (f) granulating the milled powder and intragranular excipients (e.g. by dry granulation), and (g) adding extragranular excipients. Dry granulation may be performed, for example, by roller compaction or slugging and milling.

Another embodiment of the present invention is a pharmaceutical composition that includes (a) insulin or an insulin analog, (b) a delivery agent and (c) a gelatin, as that term is used herein (e.g. including gelatin alternatives).

Another embodiment of the present invention is a process for preparing an oral insulin pharmaceutical composition by introducing (a) a delivery agent compound and (b) insulin or an insulin analog into gelatin or a gelatin alternative. In a preferred embodiment, gelatin is optionally milled and mixed with a delivery agent. The mixture is then granulated using an aqueous dispersion of insulin or an insulin analog.

Another embodiment of the present invention is a method of solubilizing insulin or an insulin analog by introducing a delivery agent (e.g. 4-CNAB or sodium 4-CNAB) to an aqueous solution and subsequently adding insulin or an insulin analog to the delivery agent-containing solution. In one embodiment, the delivery agent is added to water, sodium hydroxide is added to increase the pH of the solution (e.g., to increase the pH to about 7 or 8), and then insulin is added to the pH-adjusted solution.

Yet another embodiment is a method of treating diabetes in a subject by administering a therapeutically effective amount of the pharmaceutical composition of the present invention to the subject. The diabetic subject can be a human suffering from Type I or Type II diabetes. Generally, the insulin preparation of the present invention does not induce any significant incidence of antibodies. Preferably, the subject is administered the pharmaceutical composition of the present invention for at least once day for at least 90 days. According to a preferred embodiment, the pharmaceutical composition is administered as adjunctive therapy to a biguanide (such as metformin). According to another preferred embodiment, the pharmaceutical composition is administered as adjunctive therapy to a biguanide (such as metformin), acarbose, a glitazone (e.g., pioglitazone), or a combination thereof.

One embodiment is a method of treating diabetes (e.g. type II diabetes) in a subject who has not sufficiently responded to metformin monotherapy, by administering a therapeutically effective amount of the pharmaceutical composition of the present invention to the subject. According to a preferred embodiment, the subject continues treatment with metformin while also being treated with the pharmaceutical composition of the present invention. According to another preferred embodiment, the pharmaceutical composition is administered as adjunctive therapy to a biguanide (such as metformin), acarbose, a glitazone (e.g., pioglitazone), or a combination thereof.

Yet another embodiment is a method of treating diabetes (e.g., Type I or Type II diabetes) in a human having a hemoglobin A1c value of at least about 8.0% by administering a therapeutically effective amount of the pharmaceutical composition of the present invention to the human. According to one embodiment, the human has a hemoglobin A1c value ranging from about 8.0 to about 9.3%. Preferably, the human is administered the pharmaceutical composition of the present invention for at least once day for at least 90 days.

DETAILED DESCRIPTION OF THE INVENTION

Definitions

Figure 1:
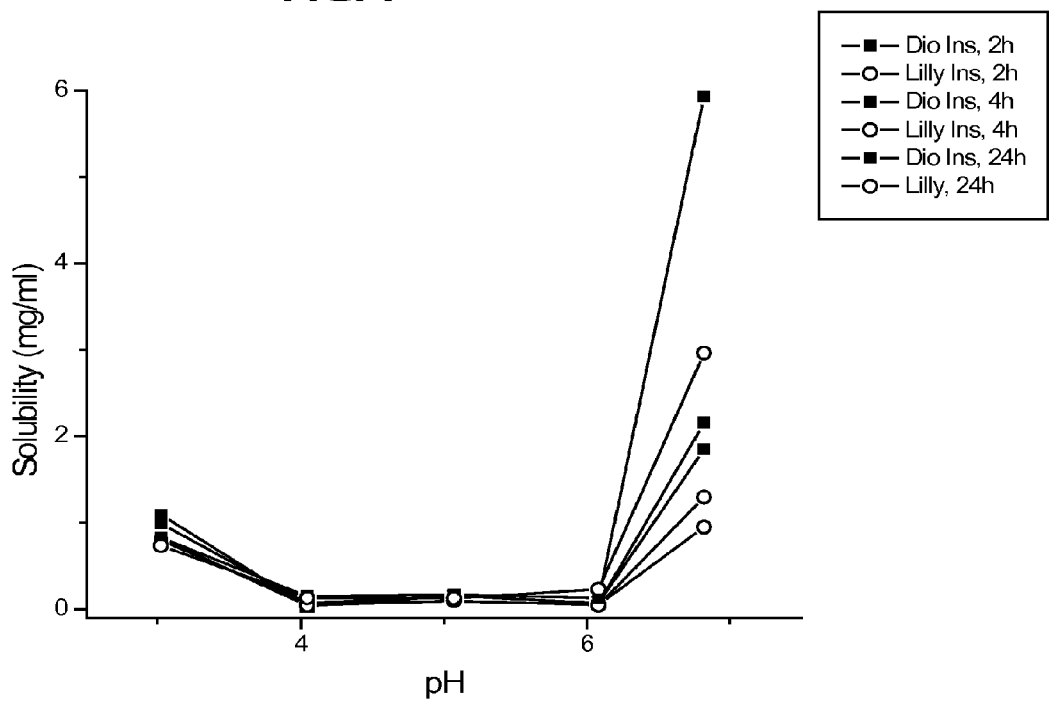
FIG. 1 sets forth the solubility of recombinant human zinc insulin at different pH and time-points.

As used herein and in the appended claims, the singular forms "a" "an" and "the" also includes plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "hydrate" as used herein includes, but is not limited to, (i) a substance containing water combined in molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of the delivery agent compound or salt thereof, or hydrate or solvate thereof.

The term "delivery agent" refers to any of the delivery agent compounds disclosed or incorporated by reference herein.

The terms "alkyl", "alkoxy", "alkylene", "alkenylene", "alkyl(arylene)", and "aryl(alkylene)" include, but are not limited to, linear and branched alkyl, alkoxy, alkylene, alkenylene, alkyl(arylene), and aryl(alkylene) groups, respectively.

Unless otherwise specified, the term "substituted" as used herein includes, but is not limited to, substitution with any one or any combination of the following substituents: halogens, hydroxide, $C_1$-$C_4$ alkyl, and $C_1$-$C_4$ alkoxy.

The term "4-MOAC" refers to 8-(N-2-hydroxy-4-methoxybenzoyl)-aminocaprylic acid and pharmaceutically acceptable salts thereof. Unless otherwise noted, the term "4-MOAC" refers to all forms of 4-MOAC, including, but not limited to, amorphous and crystalline forms of 4-MOAC.

The term "NAC" as used herein refers to N-(8-[2-hydroxybenzoyl]-amino) caprylic acid and pharmaceutically acceptable salts thereof, including its monosodium salt. Unless otherwise noted, the term "NAC" refers to all forms of NAC, including, but not limited to, all amorphous and crystalline forms of NAC. The term "SNAC" as used herein refers to the monosodium salt of NAC, including, but not limited to, all amorphous and crystalline forms of SNAC (such as those described in International Publication No. WO 2005/107462, which is hereby incorporated by reference), unless otherwise indicated.

The term "NAD" as used herein refers to N-(10-[2-hydroxybenzoyl]-amino) decanoic acid and pharmaceutically acceptable salts thereof, including, but not limited to, its monosodium salt. Unless otherwise noted, the term "NAD" refers to all forms of NAD, including, but not limited to, all amorphous and crystalline forms of NAD. The term "SNAD" as used herein refers to the monosodium salt of NAD, including, but not limited to, all amorphous and crystalline forms of SNAC.

The term "5-CNAC" refers to N-(8-[2-hydroxy-5-chlorobenzoyl]-amino)octanoic acid (also known as 8-(N-2-hydroxy-5-chlorobenzoyl)aminocaprylic acid)) and pharmaceutically acceptable salts thereof, including, but not limited to, its monosodium salt and disodium salt. Unless otherwise noted, the term "5-CNAC" refers to all forms of 5-CNAC, including, but not limited to, all amorphous and crystalline forms of it (including those described in International Publication No. WO 00/59863, PCT/US2006/036455, filed Sep. 18, 2006, and U.S. Provisional Application No. 60/718,829, filed Sep. 19, 2005, all of which are hereby incorporated by reference).

The term "4-CNAB" refers to 4-[(2-hydroxy-4-chlorobenzoyl)amino]butanoate (also known as 4-[(4-chloro-2-hydroxy-benzoyl)amino]butanoic acid) and pharmaceutically acceptable salts thereof, including, but not limited to, its monosodium salt. Unless otherwise noted, the term "4-CNAB" refers to all forms of 4-CNAB, including, but not limited to, all amorphous and crystalline forms of 4-CNAB. The term "mono-sodium 4-CNAB" refers to monosodium 4-[(2-hydroxy-4-chlorobenzoyl)amino]butanoate, including, but not limited to, anhydrous, monohydrate, and isopropanol solvates thereof and amorphous and crystalline forms thereof (including those described in International Publication Nos. WO 02/02509 and WO 03/057650, both of which is hereby incorporated by reference), unless otherwise indicated.

The term "HPOD" refers to 8-(2-hydroxyphenoxy)octyldiethanolamine and pharmaceutically acceptable salts thereof, including, but not limited to, its meslyate salt. Unless otherwise noted, the term "HPOD" refers to all forms of HPOD, including, but not limited to, all amorphous and crystalline forms of HPOD and includes anhydrous, monohydrate, and isopropanol solvates of HPOD, including those described in International Publication No. WO 2005/115406, which is hereby incorporated by reference).

The term "insulin analog" as used herein, refers to analogs of naturally occurring insulins, including human insulin or animal insulins, which differ by substitution of at least one naturally occurring amino acid residue with other amino acid residues and/or addition/removal of at least one amino acid residue from the corresponding, otherwise identical, naturally occurring insulin. Insulin analogs have a physiological effect similar to that of naturally occuring or recombinant human insulin. The added and/or replaced amino acid residues can also be those which do not occur naturally. Insulin analogs include those analogs disclosed in U.S. Pat. Nos. 6,960,561, 6,906,028, 6,852,694, 6,777,207, 6,630,348, 6,551,992, 6,534,288, 6,531,448, RE37,971, 6,465,426, 6,444,641, 6,335,316, 6,268,335, 6,051,551, 6,034,054, 5,970,973, 5,952,297, 5,922,675, 5,888,477, 5,873,358, 5,747,642, 5,693,609, 5,650,486, 5,646,242, 5,547,929, 5,504,188, 5,474,978, 5,461,031, 5,135,866, 4,421,685, all of which are hereby incorporated by reference.

The term "subject" as used herein includes a mammal, preferably a human. It may also mean other animals, including other mammals, but especially birds, poultry or other avian forms.

The phrase "pharmaceutically acceptable" refers to components or compositions that are physiologically tolerable.

The term "treating" or "treatment" of a state, disorder or condition includes:

(1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

The benefit to a subject to be treated is either statistically significant or at least perceptible to the subject or to the physician.

The term "mean", when preceding a pharmacokinetic value (e.g., mean peak) represents the arithmetic mean value of the pharmacokinetic value unless otherwise specified.

The term "Serum Concentration" or "Serum Concentration Curve" is the graphic representation of the amount of drug in an animal's (including humans) plasma at particular points in time.

The term "Area Under the Curve" or "Area Under the Concentration Curve" or "AUC" means the area present beneath the line of the graphical representation of plasma concentrations versus time in subject(s). Unless otherwise specified, AUC refers to the AUC obtained based on baseline adjusted concentrations, i.e., concentrations obtained after subtracting the individual baseline from each individual time point ($C_t$-$C_0$).

The term "Cmax" refers to the maximum observed concentration taken directly from the plasma concentration-time course profile. Unless otherwise specified, Cmax refers to Cmax obtained based on baseline adjusted concentrations, i.e., concentrations obtained after subtracting the individual baseline from each individual time point ($C_t$-$C_0$).

Delivery Agent Compounds

In one embodiment of the present invention, the delivery agent compound has the following structure, or a pharmaceutically acceptable salt thereof:

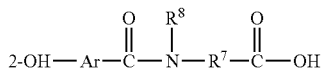

Formula A wherein

Ar is phenyl or naphthyl;

Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;

$R^7$ is $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl)naphthyl, phenyl($C_1$-$C_{10}$ alkyl), phenyl($C_1$-$C_{10}$ alkenyl), naphthyl($C_1$-$C_{10}$ alkyl), or naphthyl($C_1$-$C_{10}$ alkenyl);

$R^8$ is hydrogen, $C_1$ to $C_4$ alkyl, $C_2$ to $C_4$ alkenyl, $C_1$ to $C_4$ alkoxy, or $C_1$-$C_4$ haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, —$CO_2R_9$, or any combination thereof;

$R^9$ is hydrogen, $C_1$ to $C_4$ alkyl, or $C_2$ to $C_4$ alkenyl; and $R^7$ is optionally interrupted by oxygen, nitrogen, sulfur or any combination thereof.

In one embodiment, the delivery agent compounds are not substituted with an amino group in the position alpha to the acid group.

Suitable delivery agent compounds include, but are not limited to, N-(8-[2-hydroxybenzoyl]-amino)caprylic acid and salts thereof, e.g., a sodium salt of N-(8-[2-hydroxybenzoyl]-amino)caprylic acid, such as a mono- or di-sodium salt, N-(8-[2-hydroxybenzoyl]-amino)decanoic acid and pharmaceutically acceptable salts thereof, including its monosodium salt, 4-[(4-chloro-2-hydroxy-benzoyl)amino]butanoic acid (also known as 4-[(2-hydroxy-4-chlorobenzoyl)amino]butanoate) and pharmaceutically acceptable salts thereof, including its sodium salt (e.g., monosodium salt), N-(8-[2-hydroxy-5-chlorobenzoyl]-amino)octanoic acid (also known as 8-(N-2-hydroxy-5-chlorobenzoyl)aminocaprylic acid)) and pharmaceutically acceptable salts thereof, including its monosodium salt, and 8-(N-2-hydroxy-4-methoxybenzoyl)-aminocaprylic acid and pharmaceutically acceptable salts thereof, including its monosodium salt.

According to one embodiment, $R^7$ in Formula A is selected from $C_8$-$C_{20}$ alkyl, $C_8$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl)naphthyl, phenyl($C_1$-$C_{10}$ alkyl), phenyl ($C_1$-$C_{10}$ alkenyl), naphthyl($C_1$-$C_{10}$ alkyl), and naphthyl($C_1$-$C_{10}$ alkenyl).

According to another embodiment, $R^7$ in Formula A is selected from $C_8$-$C_{20}$ alkyl, and $C_8$-$C_{20}$ alkenyl.

In another embodiment of the present invention, the delivery agent compound has the following structure, or a pharmaceutically acceptable salt thereof:

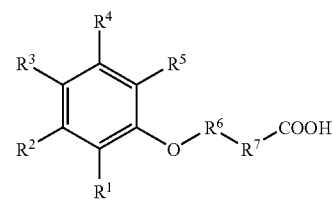

Formula B wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}(R^{12})$;

$R^5$ is H, —OH, —$NO_2$, halogen, —$CF_3$, —$NR^{14}R^{15}$, —$N^+R^{14}$, $R^{15}$, $R^{16}(R_{13})$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R_8$;

$R^6$ is optionally interrupted by O or N;

$R^7$ is a bond or arylene;

$R^7$ is optionally substituted with —OH, halogen, —C(O)CH$_3$, —NR$^{10}$R$^{11}$, or —N$^+$R$^{10}$R$^{11}$R$^{12}$(R$^{13}$)$^-$;

each occurrence of R$^8$ is independently H, C$_1$-C$_4$ alkyl, C$_2$-C$_4$ alkenyl, or —NH$_2$;

R$^9$, R$^{10}$, R$^{11}$, and R$^{12}$ independently H or C$_1$-C$_{10}$ alkyl;

R$^{13}$ is a halide, hydroxide, sulfate, tetrafluoroborate, or phosphate;

R$^{14}$, R$^{15}$ and R$^{16}$ are independently H, C$_1$-C$_{10}$ alkyl, C$_1$-C$_{10}$ alkyl substituted with —COOH, C$_2$-C$_{12}$ alkenyl, C$_2$-C$_{12}$ alkenyl substituted with —COOH, or —C(O)R$^{17}$;

R$^{17}$ is —OH, C$_1$-C$_{10}$ alkyl, or C$_2$-C$_{12}$ alkenyl; and

R$^{18}$ is H, C$_1$-C$_6$ alkyl, —OH, —NR$_{14}$R$_{15}$, or N$^+$R$^{14}$R$^{15}$R$^{16}$(R$^{13}$)$^-$.

In one particular embodiment, when R$^1$, R$^2$, R$^3$, R$^4$, and R$^5$ are H, and R$^7$ is a bond then R$^6$ is not a C$_1$-C$_6$, C$_9$ or C$_{10}$ alkyl.

In another embodiment, when R$^1$, R$^2$, R$^3$, and R$^4$ are H, R$^5$ is —OH, and R$^7$ is a bond then R$^6$ is not a C$_1$-C$_3$ alkyl.

In yet another embodiment, when at least one of R$^1$, R$^2$, R$^3$, and R$^4$ is not H, R$^5$ is —OH, and R$^7$ is a bond, then R$^6$ is not a C$_1$-C$_4$ alkyl.

In yet another embodiment, when R$^1$, R$^2$, and R$^3$ are H, R$^4$ is —OCH$_3$, R$^5$ is —C(O)CH$_3$, and R$^6$ is a bond then R$^7$ is not a C$_3$ alkyl.

In yet another embodiment, when R$^1$, R$^2$, R$^4$, and R$^5$ are H, R$^3$ is —OH, and R$^7$ is a bond then R$^6$ is not a methyl.

In yet another embodiment, R$^6$ of Formula B is a C$_8$-C$_{12}$ alkylene, C$_8$-C$_{12}$ alkenylene, or arylene.

In yet another embodiment of the present invention, the delivery agent compound has the following structure or a pharmaceutically acceptable salt thereof:

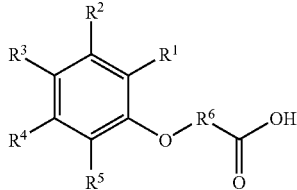

Formula C wherein
R$^1$, R$^2$, R$^3$, R$^4$ and R$^5$ are independently H, —CN, —OH, —OCH$_3$, or halogen, at least one of R$^1$, R$^2$, R$^3$, R$^4$ and R$^5$ being —CN; and R$^6$ is a C$_1$-C$_{12}$ linear or branched alkylene, a C$_1$-C$_{12}$ linear or branched alkenylene, a C$_1$-C$_{12}$ linear or branched arylene, an alkyl(arylene) or an aryl(alkylene).

According to one embodiment, when R$^1$ is —CN, R$^4$ is H or —CN, and R$^2$, R$^3$, and R$^5$ are H, then R$^6$ is not methylene ((CH$_2$)$_1$).

In another embodiment, R$^6$ of Formula C is a C$_8$-C$_{12}$ linear or branched alkylene, a C$_8$-C$_{12}$ linear or branched alkenylene, an arylene, an alkyl(arylene) or an aryl(alkylene).

In yet another embodiment, R$^6$ of Formula C is a C$_8$-C$_{12}$ linear or branched alkylene, a C$_8$-C$_{12}$ linear or branched alkenylene.

Other suitable delivery agent compounds are disclosed in U.S. Pat. No. 6,627,228, which is hereby incorporated by reference.

The delivery agent compound can also be a a polymeric delivery agent comprising a polymer conjugated to a modified amino acid or derivative thereof via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond. In one embodiment, the polymeric delivery agent is not a polypeptide or polyamino acid. In another embodiment, the modified amino acid has the structure of formula A, B, or C. In one embodiment, the polymeric delivery agent includes a modified amino acid having the structure:

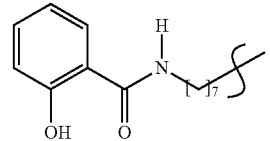

Formula D which is conjugated via a —COO group to a polymer having monomers derived from polyethylene glycol.

In one embodiment, the polymeric delivery agent is a modified amino acid having the structure of Formula D conjugated via a —COO group to a polymer having the structure:

wherein
x is from 1-14; and
Y is H or CH$_3$.

According to another embodiment, the polymeric delivery agent is compound having the structure of Formula D conjugated via a —COO group to a polymer having the structure:

wherein
x is 1-5; and
Y is CH$_3$ or H.

For example, the polymeric delivery agent can be 8-(2-hydroxybenzoylamino)-octanoic acid 2-{2-[2-(2-{2-[2-(2-methoxyethoxy)ethoxy]ethoxy}-ethoxy)ethoxy]ethoxy}ethyl ester.

Other suitable delivery agent compounds include compounds of the formula below and pharmaceutically acceptable salts thereof:

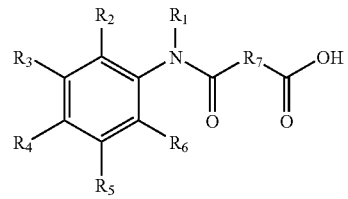

Formula E

R$_1$ is —(CH$_2$)$_m$—R$_8$, wherein m is 0 or 1;
R$_2$-R$_6$ are independently selected from hydrogen, hydroxyl, halogen, C$_1$-C$_4$ alkyl, C$_2$-C$_4$ alkenyl, C$_2$-C$_4$ alkynyl, C$_1$-C$_4$ alkoxy, and cyano;
R$_7$ is selected from C$_1$-C$_{10}$ alkyl, C$_2$-C$_{10}$ alkenyl, and C$_2$-C$_{10}$ alkynyl;
R$_8$ is selected from cyclopentyl, cyclohexyl and phenyl, wherein when R$_8$ is phenyl, m is 1; and
R$_8$ is optionally substituted with C$_1$-C$_4$ alkyl, C$_1$-C$_4$ alkoxy, halogen or hydroxyl, or a combination thereof.

Other delivery agent compounds of the present invention include those of the formula:

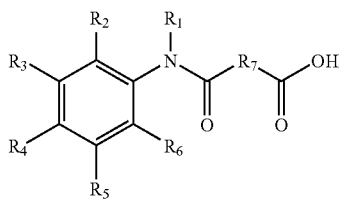

Formula F

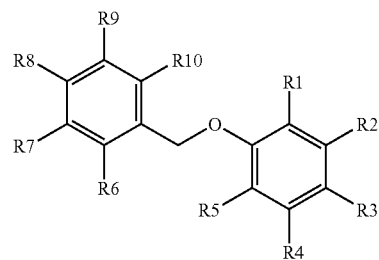

Formula I and pharmaceutically acceptable salts thereof, wherein:

$R_1$ is a $C_1$-$C_6$ alkyl, or $C_2$-$C_6$ alkenyl, $R_2$-$R_6$ are independently selected from hydrogen, hydroxyl, halogen, $C_1$-$C_4$ alkyl, $C_2$-$C_4$ alkenyl, $C_2$-$C_4$ alkynyl, $C_1$-$C_4$ alkoxy, and cyano, and $R_7$ is selected from $C_1$-$C_{10}$ alkyl, $C_2$-$C_{10}$ alkenyl, and $C_2$-$C_{10}$ alkynyl.

Other suitable delivery agent compounds include those of the formula:

and pharmaceutically acceptable salts thereof, wherein
one of $R^1$ to $R^5$ is —$(CH_2)_n$—COOH where n is 0-6; and
the remaining four members of $R^1$ to $R^5$ are independently hydrogen, $C_1$ to $C_4$ alkyl, $C_2$ to $C_4$ alkenyl, halogen, $C_1$ to $C_4$ alkoxy, or hydroxyl; and
$R_6$-$R_{10}$ are independently hydrogen, $C_1$ to $C_4$ alkyl, $C_2$ to $C_4$ alkenyl, halogen, $C_1$ to $C_4$ alkoxy, or hydroxyl.

Other delivery agents of the present invention include compounds represented by the formula:

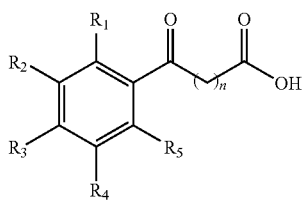

Formula G

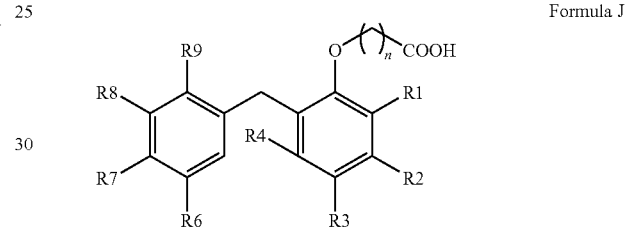

Formula J and pharmaceutically acceptable salts thereof, wherein
n is 1 to 9, and
$R^1$ to $R^5$ are independently hydrogen, $C_1$ to $C_6$ alkyl, $C_1$ to $C_6$ alkoxy, $C_2$ to $C_6$ alkenyl, halogen, hydroxyl, —NH—C(O)—CH$_3$, or —O—C$_6$H$_5$.

In one embodiment, $R^1$ to $R^5$ of Formula G are independently hydrogen, $C_1$ to $C_4$ alkyl, $C_1$ to $C_4$ alkoxy, $C_2$ to $C_4$ alkenyl, halogen, or hydroxyl.

Other suitable delivery agent compounds include those of the formula:

and pharmaceutically acceptable salts thereof, wherein
n is 1 to 9; and $R_1$ to $R_9$ are independently hydrogen, $C_1$ to $C_4$ alkyl, $C_2$ to $C_4$ alkenyl, halogen, $C_1$ to $C_4$ alkoxy, or hydroxyl.

Other suitable delivery agent compounds include those of the formula:

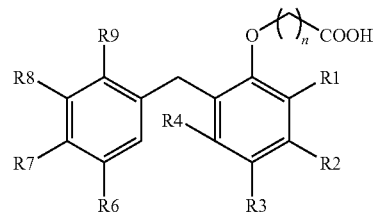

Formula K

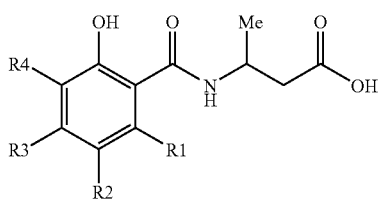

Formula H and pharmaceutically acceptable salts thereof, wherein
$R^1$ to $R^4$ are independently hydrogen, $C_1$ to $C_4$ alkyl, $C_2$ to $C_4$ alkenyl, halogen, $C_1$ to $C_4$ alkoxy, or hydroxyl.

Other delivery agent compounds of the present invention include those of the formula:

and pharmaceutically acceptable salts thereof, wherein
$R^1$-$R^5$ are independently hydrogen, $C_1$ to $C_4$ alkyl, $C_2$ to $C_4$ alkenyl, halogen, $C_1$ to $C_4$ alkoxy, hydroxyl, or —O—(CH$_2$)$_n$—COOH (where n is 1 to 12);
at least one of $R^1$ to $R^5$ is —O—(CH2)$_n$COOH where n is 1-12; and
$R^6$-$R^{10}$ are independently hydrogen, $C_1$ to $C_4$ alkyl, $C_2$ to $C_4$ alkenyl, halogen, $C_1$ to $C_4$ alkoxy, or hydroxyl.

Suitable delivery agents are described in International Publication Nos. WO 2005/117854 and WO 2005/112633, both of which were filed May 16, 2005 and their priority documents, U.S. Provisional Application Nos. 60/576,088, filed Jun. 1, 2004, U.S. Provisional Application No. 60/576, 397, filed Jun. 1, 2004, U.S. Provisional Application No. 60/576,105, filed Jun. 1, 2004, U.S. Provisional Application No. 60/571,090, filed May 14, 2004, U.S. Provisional Application No. 60/571,092, filed May 14, 2004, U.S. Provisional Application No. 60/571,195, filed May 14, 2004, U.S. Provisional Application No. 60/571,194, filed May 14, 2004, U.S. Provisional Application No. 60/571,093, filed May 14, 2004, U.S. Provisional Application No. 60/571,055, filed May 14, 2004, U.S. Provisional Application No. 60/571,151, filed May 14, 2004, U.S. Provisional Application No. 60/571,315, filed May 14, 2004, U.S. Provisional Application No. 60/571,144, filed May 14, 2004, and U.S. Provisional Application 60/571,089, filed May 14, 2004, all of which are hereby incorporated by reference in their entirety.

Other suitable delivery agents include those having the following structure and pharmaceutically acceptable salts thereof:

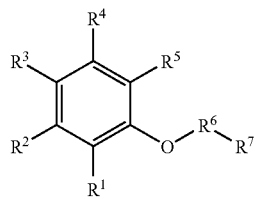

Formula L wherein
(a) $R^1$, $R^2$, $R^3$, and $R^4$ are independently H, —OH, halogen, $C_1$-$C_4$ alkyl, $C_1$-$C_4$ alkenyl, $C_1$-$C_4$ alkoxy, —C(O)$R^8$, —NO$_2$, —NR$^9$R$^{10}$, or —N$^+$R$^9$R$^{10}$R$^{11}$(Y$^-$);
$R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —NR$^{14}$R$^{15}$;
$R^9$, $R^{10}$, and $R^{11}$ are independently hydrogen, oxygen, $C_1$-$C_4$ alkyl unsubtituted or substituted with halogen or —OH, $C_2$-$C_4$ alkenyl unsubstituted or substituted with halogen or —OH;
Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;
$R^5$ is H, —OH, —NO$_2$, halogen, CF$_3$, —NR$^{14}$R$^{15}$, —N$^+$R$^{14}$R$^{15}$R$^{16}$(Y$^-$), amide, $C_1$-$C_{12}$ alkoxy, $C_1$-$C_{12}$ alkyl, $C_2$-$C_{12}$ alkenyl, carbamate, carbonate, urea, or —C(O)R$^{22}$; $R^5$ is optionally substituted with halogen, —OH, —SH, or —COOH; $R^5$ is optionally interrupted by O, N, S, or —C(O)—;
$R^{14}$, $R^{15}$, and $R^{16}$ are independently H or $C_1$-$C_{10}$ alkyl;
$R^{22}$ is H, $C_1$-$C_6$ alkyl, —OH, —NR$^{14}$R$^{15}$;
$R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl) arylene or aryl($C_1$-$C_{16}$ alkylene); $R^6$ is optionally substituted with $C_1$-$C_7$ alkyl or $C_1$-$C_7$ cycloalkyl;
$R^7$ is —NR$^{18}$R$^{19}$ or N$^+$R$^{18}$R$^{19}$R$^{20}$Y$^-$;
$R^{18}$ and $R^{19}$ are independently hydrogen, oxygen, hydroxy, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxyccarbonyl, or substituted or unsubstituted $C_5$-$C_7$ heterocyclic ring (i.e., 5, 6, or 7-membered heterocyclic ring), wherein the substitutions may be halogen or —OH; and
$R^{20}$ is independently hydrogen, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy) carbonyl), or substituted or unsubstituted aryloxycarbonyl; or
(b) $R^1$-$R^{16}$ and $R^{20}$ are as defined above; and
$R^{18}$ and $R^{19}$ combine to form a 5, 6, or 7-membered heterocyclic ring optionally interrupted with an oxo group and unsubstituted or substituted with $C_1$-$C_6$ alkyl, $C_1$-$C_6$ alkoxy, aryl, aryloxy, or carbocyclic ring.

According to one embodiment, $R^7$ is morpholino, morpholinium salt, or diethanolamino.

According to another embodiment, $R^6$ is a $C_1$-$C_{16}$ alkylene and $R^7$ is morpholino or a morpholinium salt. Preferably, $R^6$ is $C_4$-$C_{12}$ alkylene, such as an unsubstituted $C_4$-$C_{12}$ alkylene. More preferably, $R^6$ is $C_4$-$C_{10}$, $C_4$-$C_8$, or $C_6$-$C_8$ alkylene, such as an unsubstituted $C_4$-$C_{10}$, $C_4$-$C_8$, or $C_6$-$C_8$ alkylene. According to one embodiment, one of $R^1$-$R^5$ is hydroxy, for example, $R^1$ can be hydroxy.

According to yet another embodiment, when $R^6$ is a $C_1$-$C_{10}$ alkylene, at most one of $R^2$ and $R^4$ is halogen. According to another embodiment, $R^6$ is a $C_8$-$C_{16}$, $C_9$-$C_{16}$, $C_{10}$-$C_{16}$, or $C_{11}$-$C_{16}$ alkylene. For instance, $R^6$ may be a $C_8$, $C_9$, $C_{10}$, $C_{11}$, or $C_{12}$ alkylene (e.g., a normal $C_8$-$C_{12}$ alkylene). According to yet another embodiment, at most one of $R^1$ and $R^5$ is alkyl.

According to yet another embodiment, $R^1$ is hydroxy and $R^2$, $R^3$, $R^4$, and $R^5$ are independently hydrogen or halogen.

According to yet another embodiment, $R^2$ is hydroxy and $R^1$, $R^3$, $R^4$, and $R^5$ are independently hydrogen or halogen.

According to yet another embodiment, $R^3$ is hydroxy and $R^1$, $R^2$, $R^4$, and $R^5$ are independently hydrogen or halogen.

In a preferred embodiment, halogen is F, Cl or Br, more preferably F or Cl, and even more preferably Cl.

According to yet another embodiment, $R^6$ is $C_1$-$C_{16}$ alkylene, ($C_1$-$C_{16}$ alkyl) arylene or aryl($C_1$-$C_{16}$ alkylene). More preferably $R^6$ is $C_1$-$C_{12}$ alkylene, more preferably $C_3$-$C_{10}$ alkylene, more preferably $C_4$-$C_{10}$ or $C_4$-$C_8$ alkylene, and more preferably $C_6$-$C_8$ alkylene. More preferably, $R^6$ is unsubstituted.

According to yet another embodiment, $R^7$ is —NR$^{18}$R$^{19}$ and $R^{18}$ and $R^{19}$ are independently $C_1$-$C_4$ alkyl (e.g., methyl, ethyl, propyl, or butyl) substituted with —OH. In another embodiment, $R^7$ is —NR$^{18}$R$^{19}$ and $R^{18}$ and $R^{19}$ combine to form a six membered heterocyclic ring substituted with an oxo group.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene, and $R^7$ wherein $R^{18}$ and $R^{19}$ combine to form a 5, 6 or 7 membered heterocyclic ring.

According to another preferred embodiment, one of $R^3$, $R^4$, and $R^5$ is hydroxy and the others are independently halogen or hydrogen; $R^1$ and $R^2$ are independently halogen or hydrogen; $R^6$ is $C_1$-$C_{16}$ alkylene; and $R^7$ is $NR^{18}R^{19}$ wherein $R^{18}$ and $R^{19}$ combine to form a 5, 6, or 7 membered heterocyclic ring. $R^6$ is preferably $C_6$-$C_{16}$, $C_6$-$C_{10}$, $C_8$-$C_{16}$, $C_{10}$-$C_{16}$, or $C_4$-$C_8$ alkylene, such as unsubstituted $C_6$-$C_{16}$, $C_6$-$C_{10}$, $C_8$-$C_{16}$, $C_{10}$-$C_{16}$, or $C_4$-$C_8$ alkylene. Preferably, $R^{18}$ and $R^{19}$ form a morpholino or imidazole.

In another preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene; and $R^7$ is $N^+R^{18}R^{19}R^{20}(Y^-)$ wherein $R^{18}$ and $R^{19}$ are hydroxy substituted $C_1$-$C_{16}$ alkyl and $R^{20}$ is hydrogen.

In another preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene; and $R^7$ is $N^+R^{18}R^{19}R^{20}(Y^-)$ wherein $R^{18}$ and $R^{19}$ are hydroxy substituted $C_1$-$C_{16}$ alkyl and $R^{20}$ is hydrogen.

In another preferred embodiment, $R^1$, $R^2$, $R^4$, $R^5$ are independently halogen or hydrogen; $R^3$ is —OH, or —OCH$_3$; and $R^7$ is $N^+R^{18}R^{19}R^{20}(Y^-)$ wherein $R^{18}$ and $R^{19}$ are hydroxy substituted $C_1$-$C_{16}$ alkyl and $R^{20}$ is hydrogen.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_6$ alkylene or aryl substituted $C_1$-$C_{12}$ alkyl; and $R^7$ is —NR$^{18}$R$^{19}$ wherein $R^{18}$ and $R^{19}$ combine to form a 5, 6, or 7 membered heterocyclic ring or $N^+R^{18}R^{19}R^{20}(Y^-)$ wherein $R^{18}$ and $R^{19}$ are hydroxy substituted $C_1$-$C_{16}$ alkyl and $R^{20}$ is hydrogen.

In another preferred embodiment, the citrate salt of the delivery agent is used.

Other suitable delivery agents include those having the following structure and pharmaceutically acceptable salts thereof:

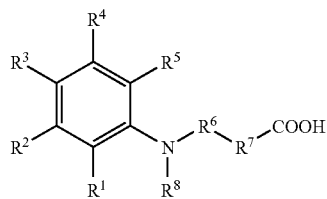

Formula M wherein
$R^1$, $R^2$, $R^3$, and $R^4$ are independently H, —OH, halogen, —OCH$_3$, —NR$^{10}$R$^{11}$ or —N$^+$R$^{10}$R$^{11}$R$^{12}$ (R$^{13}$)$^-$;
$R^5$ is H, —OH, —NO$_2$, —NR$^{14}$R$^{15}$, —N$^+$R$^{14}$R$^{15}$R$^{16}$ (R$^{13}$)$^-$, amide, $C_1$-$C_{12}$ alkyl, $C_2$-$C_{12}$ alkenyl, carbamate, carbonate, urea, or —C(O)R$^{18}$;
$R^5$ is optionally substituted with —OH, —SH, or —COOH;
$R^5$ is optionally interrupted by O, N, S, or —C(O)—;
$R^6$ is a $C_1$-$C_{12}$ alkylene, $C_1$-$C_{12}$ alkenylene, or arylene;
$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^9$;
$R^6$ is optionally interrupted by O or N;
$R^7$ is a bond or arylene;
$R^7$ is optionally substituted with —OH, halogen, —C(O)CH$_3$, —NR$^{10}$R$^{11}$ or —N$^+$R$^{10}$R$^{11}$R$^{12}$(R$^{13}$)$^-$;

$R^8$ is H or $C_1$-$C_4$ alkyl;
$R^9$ is H, $C_1$-$C_4$ alkyl, or $C_2$-$C_4$ alkenyl;
$R^{10}$, $R^{11}$, and $R^{12}$ are independently H or $C_1$-$C_{10}$ alkyl;
$R^{13}$ is a halide, hydroxide, sulfate, tetrafluoroborate, or phosphate;
$R^{15}$, and $R^{16}$ are independently H, $C_1$-$C_{10}$ alkyl, $C_2$-$C_{12}$ alkenyl, O, or —C(O)R$^{17}$;
$R^{17}$ is —OH, $C_1$-$C_{10}$ alkyl, or $C_2$-$C_{12}$ alkenyl; and
$R^{18}$ is —OH, $C_1$-$C_6$ alkyl, —NR$^{14}$R$^{15}$, —N$^+$R$^{14}$R$^{15}$R$^{16}$ (R$^{13}$)$_-$.

According to one embodiment, when $R^5$ is OCH$_3$ then $R^6$ is $C_1$-$C_8$ or $C_{10}$-$C_{12}$ alkyl.

According to a preferred embodiment, $R^5$ is not —OCH$_3$. More preferably, $R^5$ is not alkoxy.

According to another preferred embodiment, $R^1$, $R^2$, $R^3$, and $R^4$ are hydrogen, $R^5$ is —COOH, —C(O)NH$_2$, —C(O) CH$_3$, or —NO$_2$, $R^6$ is —(CH$_2$)$_7$—, and $R^7$ is a bond.

According to yet another preferred embodiment, $R^1$, $R^2$, $R^3$, and $R^4$ are hydrogen, $R^5$ is —C(O)NH$_2$, $R^6$ is —CH$_2$—, and $R^7$ is a para-phenylene.

According to one embodiment, the delivery agents of formula (6) have the formula:

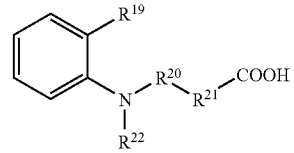

Formula N wherein
$R^{19}$ is —NO$_2$ or —C(O)R$^{23}$;
$R^{20}$ is a $C_1$-$C_{12}$ alkylene or $C_1$-$C_{12}$ alkenylene;
$R^{21}$ is a bond or arylene;
$R^{22}$ is H or $C_1$-$C_4$ alkyl; and
$R^{23}$ is —OH, $C_1$-$C_6$ alkyl, or —NH$_2$.

The delivery agent compound can also be any of those described in U.S. Pat. Nos. 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516; International Publication Nos. WO94/23767, WO95/11690, WO95/28920, WO95/28838, WO96/10396, WO96/09813, WO96/12473, WO97/36480, WO 2004/104018, WO 2004080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/21951, WO 97/47288, WO 97/31938, WO 97/10197, WO 96/40076, WO 96/40070, WO 96/39835, WO 96/33699, WO 96/30036, WO 96/21464, WO 96/12475, and WO 96/12474; and U.S. Published Application Nos. 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Each of the above listed U.S. patents and U.S. and International published applications are herein incorporated by reference.

Non-limiting examples of delivery agent compounds include N-(8-[2-hydroxybenzoyl]-amino)caprylic acid, N-(10-[2-hydroxybenzoyl]-amino)decanoic acid, 8-(2-hydroxy-4-methoxybenzoylamino)octanoic acid, 8-(2,6-dihydroxybenzoylamino)octanoic acid, 8-(2-hydroxy-5-bromobenzoylamino)octanoic acid, 8-(2-hydroxy-5-chlorobenzoylamino)octanoic acid, 8-(2-hydroxy-5-iodobenzoylamino)octanoic acid, 8-(2-hydroxy-5-methylbenzoylamino)octanoic acid, 8-(2-hydroxy-5-fluorobenzoylamino)octanoic acid, 8-(2-hydroxy-5-methoxybenzoylamino)octanoic acid, 8-(3-hydroxyphenoxy)octanoic acid, 8-(4-hydroxyphenoxy)octanoic acid, 6-(2-cyanophenoxy)hexanoic acid, 8-(2-Hydroxyphenoxy)octyl-diethanolamine, 8-(4-hydroxyphenoxy)octanoate, 8-(4-hydroxyphenoxy)octanoate, 8-(2-hydroxy-4-methoxybenzoylamino)octanoic acid, 8-(2-hydroxy-5-methoxybenzoylamino)-octanoic acid, and salts thereof. Preferred salts include, but are not limited to, pharmaceutically acceptable salts thereof such as the monosodium and disodium salts.

The delivery agent compounds may be in the form of the carboxylic acid or pharmaceutically acceptable salts thereof, such as sodium salts, and hydrates and solvates thereof. The salts may be mono- or multi-valent salts, such as monosodium salts and disodium salts. The delivery agent compounds may contain different counter ions chosen for example due to their effect on modifying the dissolution profile of the carrier.

The delivery agent compounds may be prepared by methods known in the art, such as those discussed in the aforementioned publications (e.g., International Publication Nos. WO 98/34632, WO 00/07979, WO 01/44199, WO 01/32596, WO 02/20466, and WO 03/045306). SNAC, SNAD, and the free acid and other salts thereof may be prepared by methods known in the art, such as those described in U.S. Pat. Nos. 5,650,386 and 5,866,536.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Solutions Containing a Delivery Agent Compound and Insulin or an Analog thereof

Some processes of the present invention involve the introduction of a delivery agent and insulin into an aqueous solution and obtaining a powder from this solution (e.g. by lyophillization or rotary evaporation). Generally water is used as the solvent, although the solvent can also comprise or consist essentially of other solvents which dissolve the delivery agent (e.g. sodium 4-CNAB) and insulin. For example, ethanol, methanol, isopropyl alcohol, tetrahydrofuran, dioxane, butanol, acetone, 2-butanone, methyl tert-butyl ether, n-propanol, methylene chloride, and other similar low boiling point solvents could be used in lieu of, or in combination with, water.

Once obtained, the powder (which contains insulin and a delivery agent compound) may be further processed (e.g. milled or granulated with other excipeints) and compressed into tablets or filled into capsules.

Gelatin Based Pharmaceutical Formulations

Gelatin is a mixture of purified protein fractions that may be obtained by partial hydrolysis of animal collagen by an acid or an alkaline. The process of acid hydrolysis is referred to as Type A and that by alkaline hydrolysis is referred to as Type B. Gelatin is a linear polymer that is comprised of amino acids which could result in a molecular weight ranging from 15,000 to 250,000. As used herein, the term gelatin includes acid and alkaline hydrolysates of animal collagen.

Gelatin may be applied in formulations of the present invention to serve many functions, such as a coating, a suspending agent, tablet binder and/or as a viscosity-increasing agent. Insulin/delivery agent tablets (e.g. insulin/sodium 4-CNAB) may be formulated at various concentrations of gelatin and at various ratios of insulin and delivery agent.

In water, gelatin swells and softens and it can absorb between 5-10 times its own weight of water. There are several hydrophilic natural and synthetic polymers may be applied, in certain embodiments, in place of gelatin. For example, (a) anionic polymers: alginic acid, dextran sulfate, pectin; (b) cationic acid: chitosan, polylysine; (c) amphiphatic polymers: carboxylmethyl chitin, fibrin; (d) neutral polymers such as dextran, agarose, pullulan.

As used herein, the term gelatin includes gelatin and gelatin alternatives disclosed in Remington's Pharmaceutical Sciences, 16th ed., Mack Publishing Company, Easton, Pa. (1980), page 1245 and pages 1576-1582, which is hereby incorporated by reference in its entirety. The term gelatin also includes compositons disclosed in U.S. Pat. No. 6,090,915, U.S. Pat. No. 4,043,996, U.S. Pat. No. 4,064,008, U.S. Pat. No. 4,176,117, U.S. Pat. No. 4,889,920, U.S. Pat. No. 4,374,063, U.S. Pat. No. 5,210,182, U.S. Pat. No. 4,232,425, U.S. Pat. No. 4,402,873, U.S. Pat. No. 4,427,583, U.S. Pat. No. 5,093,474, U.S. Pat. No. 5,288,408 and U.S. Pat. No. 5,459,241, each of which is hereby incorporated by reference in their entirety.

The term gelatin, as used herein also includes gelatin substitutes and alternatives. Generally, such a gelatin alternative can be made from easily obtainable (e.g. vegetable) materials having a homogeneous composition and having all the essential characteristics of gelatin. In the manufacture of soft gel films and capsules, the soft gel composition preferably possesses the properties of good wet and dry film strength, insolubility in cold water, oil, and alcohol, solubility in hot water, temperature and pressure sealability, film clarity, film flexibility, edibility, inertness to drugs or other materials to be encapsulated, and rapid setting from a hot liquid to form a gel.

One gelatin alternative is a film-forming composition that comprises starch material selected from modified starch and waxy starch; gum; and plasticizer as disclosed in U.S. Pat. No. 6,375,981, which is hereby incorporated by reference. The modified starch or waxy starch preferably has a dextrose equivalent (DE) of less than about 1, and more preferably has no measurable DE. This composition can be, but is not required to be, 100% gelatin-free. Thus, the composition can be used as a gelatin replacement, or as an extender in gelatin formulations.

Another gelatin alternative is wheat fiber gel as disclosed in U.S. Pat. No. 6,440,480, which is hereby incorporated by reference. Wheat fiber gel is made by thermal/physical processing of wheat fiber. A special milling technique is used for treating wheat material resulting in a product containing a large proportion of microfine particles. Specific improvements are obtained by mixing the product with maltodextrin. The product so obtained is sold under the tradename Vitacel®, by FMC Biopolymer of Philadelphia, Pa. This product is a dry powder, which readily disperses in water. Upon stirring of the dispersion the gel forms through shear forces. It is reported that wheat fiber gel can be used as a gelatin replacer in yogurt or ice cream. (I. I. Bollinger, Food Marketing & Techn. October 1995, 4-6).

Carrageenan is yet another gelatin alternative. Carrageenan is a natural hydrocolloid, a polysaccharide hydrocolloid, which is derived from seaweed. It comprises a carbohydrate polymer of repeating sugar units, which is linear, without significant numbers of branches or substitutions.

Methods of Treatment

The present invention also provides methods for treating a subject with impaired glucose tolerance or with early or late stage diabetes comprise orally administering to the mammal a pharmaceutical formulation of the present invention that includes a therapeutically effective amount of insulin or an insulin analog and a delivery agent in an amount effective to facilitate the absorption of the insulin.

The pharmaceutical formulations may also include a biguanide such as metformin, as disclosed in International Application No. PCT/US05/27499, which is hereby incorporated by reference.

It is preferred that the administration be on a chronic basis, e.g., for at least two weeks. In various embodiments, the administration is preprandially and at bedtime such that, after two weeks of treatment, the subject achieves improved glucose tolerance and glycemic control, as well as improved insulin utilization, insulin sensitivity, insulin secretion capacity and/or $HbA_1c$ levels, as compared with baseline levels prior to treatment.

Improved glucose tolerance and better endogenous capacity of the subject to handle sugar load can also be measured by an AUC of blood glucose excursion, following a glucose load, that is reduced by a statistically significant amount as compared with AUC of blood glucose excursion, following a glucose load, prior to treatment.

Improved glycemic control can be demonstrated by:
  decreased fasting blood glucose levels as measured by fasting blood glucose concentration that is reduced by a statistically significant amount as compared with baseline fasting blood glucose concentration prior to treatment.
  decreased serum fructosamine concentrations, as measured by serum fructosamine assay, that is reduced by a statistically significant amount as compared with baseline serum fructosamine concentrations prior to treatment.
  improved HbA1c levels after treatment compared with baseline levels prior to treatment. Preferably, the improved HbA1c levels are measured by a statistically significant decline in HbA1c levels. When treating a mammal with impaired glucose tolerance or with early or late stage diabetes, administration of the pharmaceutical formulation of the present invention can preferably be made to a mammal having an $HbA_{1c}$ level ranging from normal to elevated prior to treatment.

Improved insulin utilization and insulin sensitivity of the subject's body can be measured by a statistically significant decline in HOMA (Homeostasis Model Assessment). Improved insulin secretion capacity of the subject's body may also be measured by Stumvoll first-phase insulin secretion capacity index.

In preferred embodiments of the invention, by virtue of the chronic administration of oral dosage forms of the present invention, the subject achieves improved glucose tolerance and glycemic control as compared with baseline levels prior to treatment even without any statistically significant increase in weight, any statistically significant increase in risk of hypoglycemia or any statistically significant increase in risk of hyperinsulinemia in the mammal over the treatment period, and without the need for monitoring the mammal's blood glucose concentrations or $HbA_1c$ levels. Further, by virtue of the chronic administration of oral dosage forms of the present invention, the subject achieves improved insulin utilization, insulin sensitivity insulin secretion capacity and $HbA_1c$ levels as compared with baseline levels prior to treatment.

It is preferred that the administration of the oral pharmaceutical formulation is administered 1-4 or more times daily, preprandially and/or at bedtime. In one embodiment of the invention, administration of the pharmaceutical formulation takes place once daily, either at bedtime or preprandially for one meal during the day time, e.g., for breakfast, lunch or dinner. In another embodiment, administration of the pharmaceutical formulation takes place multiple times daily, preferably at bedtime and preprandially for one meal during the day time, e.g., for breakfast, lunch or dinner. In a further embodiment, administration of the pharmaceutical formulation takes place multiple times daily, preferably at bedtime and preprandially for more than one meal during the day time. Administration of the pharmaceutical formulation can also be at or shortly prior to bedtime and concurrently with or shortly prior to ingestion of each meal, i.e., within about 15 minutes or less of ingestion of each meal.

Preferably, the insulin formulations are administered to human patients on a chronic basis, e.g., for at least about two weeks. The dosage form of the present invention can be administered for at least one day, for one week, for two weeks, for longer periods, for alternating on-off time periods, or for the life of the patient.

The frequency of administration of the oral pharmaceutical formulation, on a daily basis (i.e., how often during one day-night period) and on a chronic basis (i.e., for how many days), may depend upon the patient's position along a "diabetes continuum", i.e., the extent of the patient's impaired glucose tolerance, the patient's stage of diabetes and the patient's need for exogenous glycemic control. This continuum ranges from normal glycemic control, to simple impaired glucose tolerance and insulin resistance seen in pre-diabetics or early stage type 2 diabetics, to failure of insulin production by the pancreas seen in type 1 diabetics and late stage type 2 diabetics. This can also be measured by the patient's $HbA_1c$ concentration, ranging from normal to elevated levels (e.g., a HbA1C value of 8.0% or greater).

For example, if the subject has a need for fasting glycemic control, the oral pharmaceutical formulation should preferably be administered only at or shortly prior to bedtime. If the subject has some need for post-prandial glycemic control, the oral pharmaceutical formulation should preferably be administered preprandially for some meals. If the subject has a need for total post-prandial glycemic control, the oral pharmaceutical formulation should preferably be administered preprandially for all meals. If the subject has a need for comprehensive glycemic control, the oral pharmaceutical formulation should preferably be administered preprandially for all meals and at or shortly prior to bedtime.

Embodiments of the present invention also provide a method of achieving glucose homeostasis in subjects, comprising orally administering to a subject a pharmaceutical formulation comprising a therapeutically effective amount of insulin or an insulin analog and a delivery agent in an amount effective to facilitate the absorption of the insulin or insulin analog. It is preferred that the administration be on a chronic basis, e.g., for at least two weeks, and be preprandially and at bedtime such that, after two weeks of treatment, the mammal achieves improved glucose tolerance and glycemic control as compared with baseline levels prior to treatment.

Examples

The following examples illustrate the invention without limitation. All parts are given by weight unless otherwise indicated.

Example 1

Solubilization of Insulin

The solubility of recombinant human zinc insulin obtained from Diosynth France (distributed in the U.S. through Diosynth, Inc.) (hereafter insulin type #1) and Eli Lilly Co. (hereafter insulin type #2) was determined in aqueous solutions having various pH values at 37° C. Excess insulin was added to buffer solutions at pH values of 1, 2, 3, 4, 5, 6, 6.8, and 7.4. Vials containing the solutions were shaken in a constant temperature water bath, and visually observed at regular time intervals. Samples were taken at 2 hours, 4 hours, and 24 hours and analyzed by a stability-indicating HPLC method. The results are shown below in Table 1:

Visual observation indicated that insulin type #1 dissolved faster than insulin type #2. This difference was not observed at pH 1, 2, and 7.4 where dissolution was very rapid for both insulin types. Solubility at pH 1, 2 and 7.4 was in excess of 4 mg/mL. Solubility at pH 6.8 was greater than 4 mg/mL for insulin type #1 and 2 mg/mL for insulin type #2, but complete dissolution occurred only after overnight shaking. The difference in the dissolution rate of insulin type #2 was most apparent at this pH. Both types of insulin exhibited some degradation at pH 3, 4, 5, and 6 after 24 hours of shaking. As expected, solubility was lowest around pH 5, with the solubilities at pH 4, 5, and 6 all being around 0.1 mg/mL.

The results for pH 3-6.8 are shown in FIG. 1.

Example 2

Solubilization of Insulin in Solutions Containing a Delivery Agent

The solubility of insulin was investigated in aqueous solutions containing varying amounts of the delivery agent compound sodium 4-CNAB. The aqueous solution containing delivery agent was adjusted to pH 1 by the addition of 1N HCl and excess insulin was added to the acidified solution. Thereafter, the pH of the solution was increased by the addition of increments of 1N NaOH. Vials containing the suspensions were left without shaking or sonicating for 1-2 hours. The supernatant was analyzed for insulin and sodium 4-CNAB using an HPLC method and the pH was recorded. This process was repeated with increased amounts of delivery agent added to the solution until the insulin was completely solubilized. All of these experiments were performed at room temperature. The results are set forth below in Table 2.

TABLE 2

| Delivery Agent | pH of Delivery Agent solution | Delivery Agent, (mg/mL) | Insulin, (mg/mL) |
|---|---|---|---|
| None (DI water) | 6.3 | — | 1.14 |
| 4-CNAB | 6.4 | 5 | 0.5 |
| | 6.45 | 10 | 1 |
| | 6.26 | 50 | 11 |
| | 6.49 | 50 | 44 |
| | 6.71 | 100 | 86 |
| | 6.45 | 100 | >110 |
| | 6.83 | 150 | 187 |
| | 6.79 | 200 | >135 |
| SNAC | 7.9 | 150 | >200 |
| HPOD | 3.9 | 250 | >50 |

TABLE 1 pH-solubility data of Diosynth and Lilly insulin at 37° C.

| | Insulin concentration (mg/ml), 2 h | | Insulin concentration (mg/ml), 4 h | | Insulin concentration (mg/ml), 24 h | |
|---|---|---|---|---|---|---|
| pH | insulin type # 1 | insulin type # 2 | insulin type # 1 | insulin type # 2 | insulin type # 1 | insulin type # 2 |
| 1.23 | >2, deg* | >2, deg | >4, deg | >4, deg | 0.814, deg | deg |
| 2.02 | >2, deg | >2, deg | —, deg | —, deg | >4, deg | >2, deg |
| 3.02 | 0.989, deg | 0.797, deg | 1.092, deg | 0.814, deg | 0.826, deg | 0.731, deg |
| 4.05 | 0.066 | 0.068 | 0.0317 | 0.040 | 0.147, deg | 0.128, deg |
| 5.07 | 0.156 | 0.091 | 0.155 | 0.094 | 0.165, deg | 0.124, deg |
| 6.08 | 0.066 | 0.049 | 0.0612 | 0.044 | 0.126, deg | 0.229, deg |
| 6.82 | 1.852 | 0.947 | >2 | 1.294 | >4 | >2 |
| 7.42 | >2 | >2 | >4 | >4 | >4 | >4 | deg - products of degradation present in chromatograms

Figure 2:
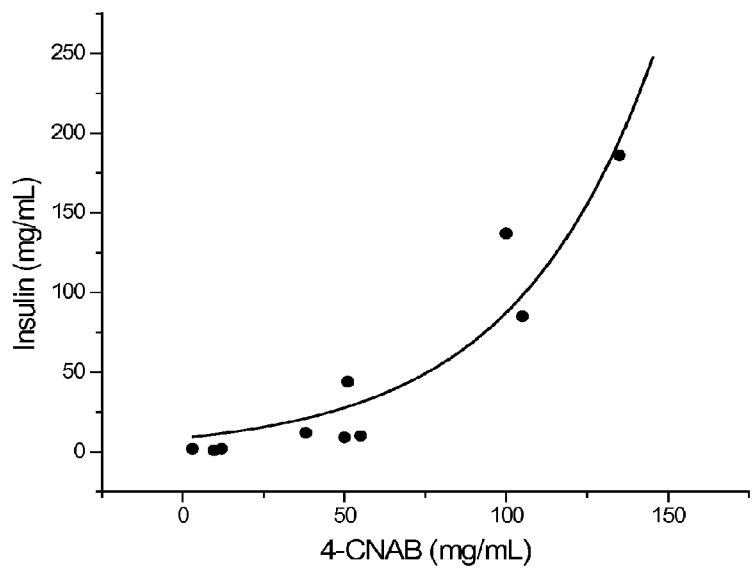
FIG. 2 sets forth a solubility curve for insulin and 4-CNAB.

The results for 4-CNAB and Insulin are also shown in FIG. 2.

Example 4

Solubilization of Insulin Tablet

Figure 3:
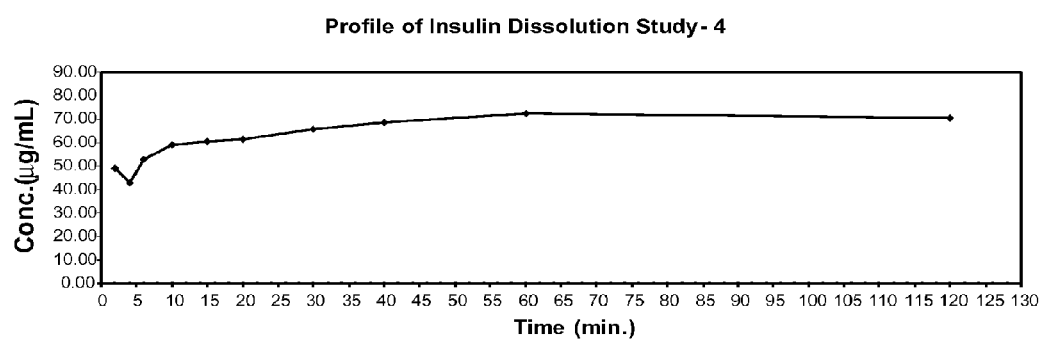
FIGS. 3 and 4 set forth insulin dissolution profiles in deionized water.
Figure 4:
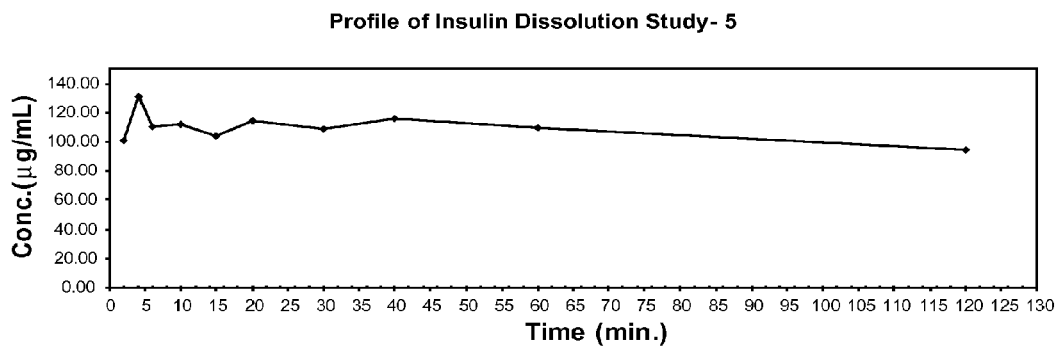

A 300 mg pellet of insulin was prepared in a die. The surface area of the pellet available to the dissolution medium was 0.484 cm². The pellet was compressed at 1200-1400 lbs on a Carver press to form discs. The die was then attached to the shaft of a dissolution apparatus (USP Dissolution Type II (Paddle) made by Vankel). The die was rotated at 100 rpm and then immersed in 500 mL of degassed dissolution medium maintained at 37° C. Dissolution experiments were conducted in water and in aqueous solutions containing sodium 4-CNAB. Samples of the solutions were taken over two hours and analyzed by HPLC. FIGS. 3 and 4 show dissolution profiles of insulin in deionized (DI) water and in 10 mg/mL sodium 4-CNAB solution, respectively.

The rate of insulin dissolution was significantly greater in the 10 mg/mL sodium 4-CNAB dissolution media than the deionized water dissolution media.

The experiments were repeated in 50 mg/ml sodium 4-CNAB dissolution media. The insulin levels in these solutions were below the detection limits of the HPLC technique used.

Example 6

Lyophilized Insulin/4-CNAB Formulations

Lyophilization as a method of co-drying insulin/4-CNAB solutions to obtain co-dried insulin/sodium 4-CNAB powder was investigated. The 3 formulations shown in Table 5 were prepared as follows.

Initially, 4-CNAB was used to solubilize the insulin. The required amounts of insulin and sodium 4-CNAB were weighed out. The sodium 4-CNAB was added to the required amount of water (about 20 ml of water per gram of sodium 4-CNAB) and stirred (1-5 minutes) until completely dissolved. The corresponding amount of insulin was then dispersed in the sodium 4-CNAB solution and left without stirring, shaking or sonicating for 0.5-2 hours until solution became clear. The solution was lyophilized using the cycle in shown in Table 4.

TABLE 4

The freeze-drying cycle for Insulin/4-CNAB solutions.

| Temperature ° C. | Time (minutes) | Pressure (Torr) |
|---|---|---|
| −10 | 30 | |
| −45 | 30 | 500 |
| −35 | 1200 | 100 |
| −35 | 240 | 50 |
| 25 | 1440 | 25 |

TABLE 5

| Components | Formulation 1 | Formulation 2 | Formulation 3 |
|---|---|---|---|
| Recombinant Human Insulin (50 Units) (Strenght: 27.5 Units/mg) | 1.8 mg | 1.8 mg | 1.8 mg |
| 4-CNAB Monosodium Salt | 80 mg | 160 mg | 240 mg |
| Dibasic Calcium Phosphate | 36 mg | 46 mg | 79.75 mg |
| Magnesium stearate | 1.2 mg | 2.2 mg | 3.55 mg |
| Total Weight/tablet | 119 mg | 210 mg | 325 mg |

Tablets were prepared by mixing the lyophilized insulin/4CNAB powder, dibasic calcium phosphate and magnesium stearate. The powder mixture was compressed into tablets using a single punch Korsch EK-0 tablet press to prepare an initial compact. Granules were obtained by crushing the initial compact in a mortar and passing the granules through a 35 mesh sieve. The granules were compressed into tablets of a predetermined weight and stored in a freezer at −20° C.

Example 7

In-Vivo Primate Studies

The formulations of Example 6 were fed to rhesus monkeys. The monkeys were fasted for at least 12 hrs prior to dosing and up to 4 hrs after dosing. Water was withheld approximately 1 hr before dosing and up to 2 hrs after dosing after which it was permitted ad libitum. The dosing was followed by a 5 ml water flush. Blood samples (approximately 2 ml each) were collected by venipuncture at 15 minutes before dosing (t=0) and at 5, 10, 15, 20, 30, 45 minutes and 1, 1.5, 2, 3, 4 hr after dosing.

Figure 5:
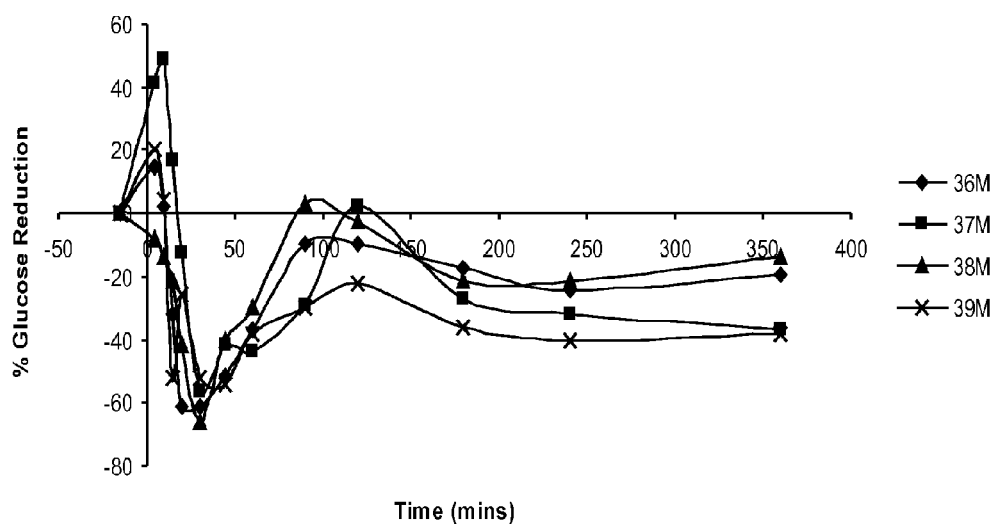
FIGS. 5-12 set forth results of insulin dosage forms administered to monkeys as described in Example 7.
Figure 6:
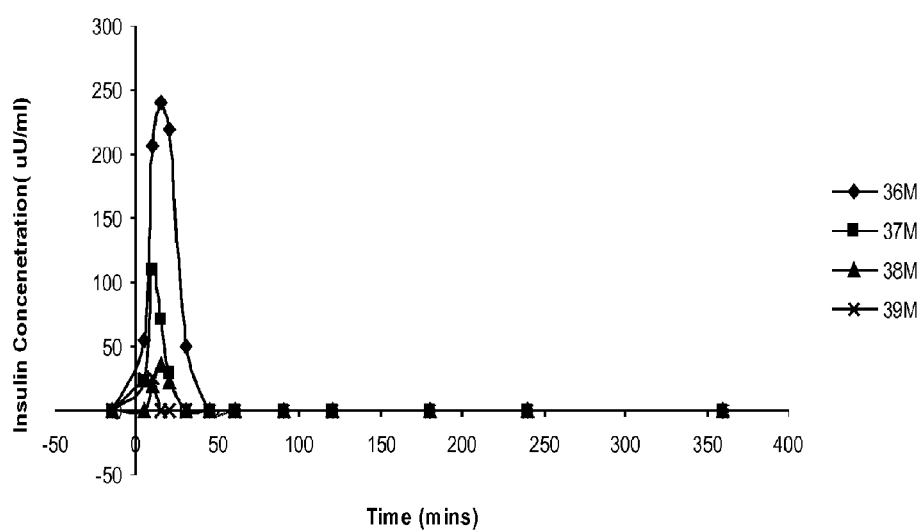
Figure 7:
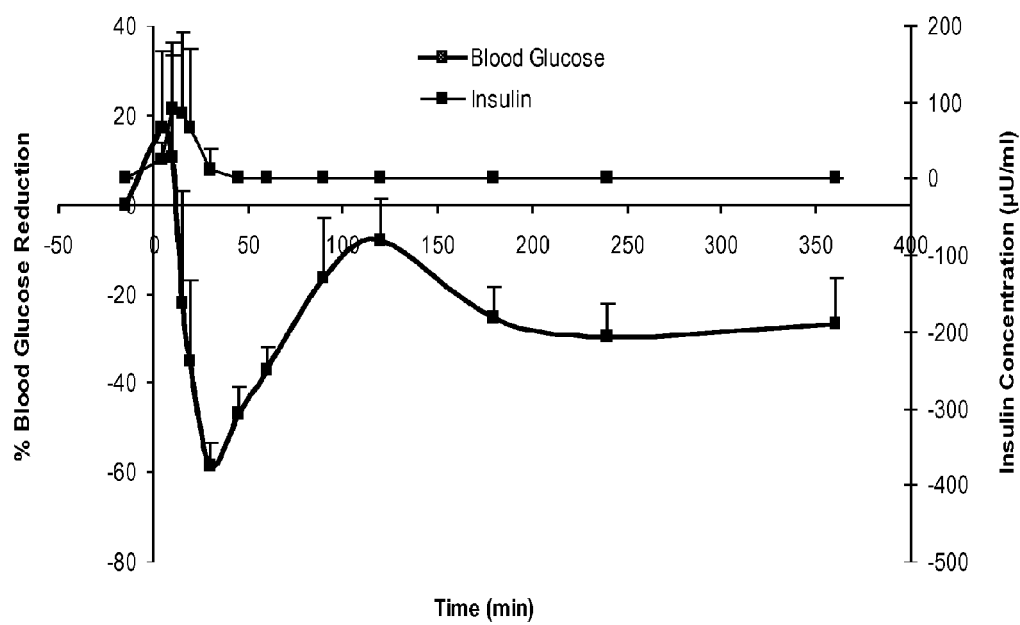
Figure 8:
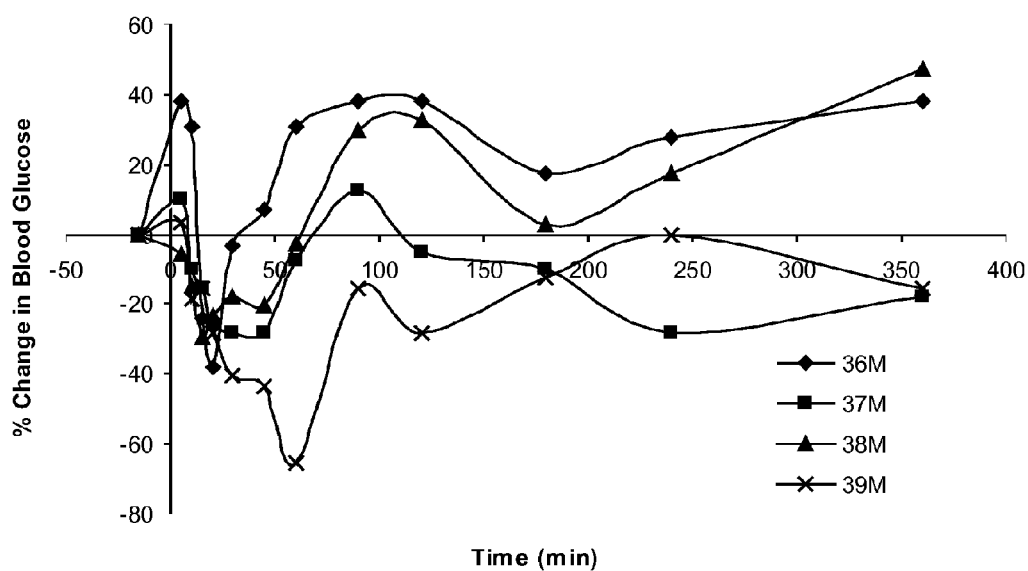
Figure 9:
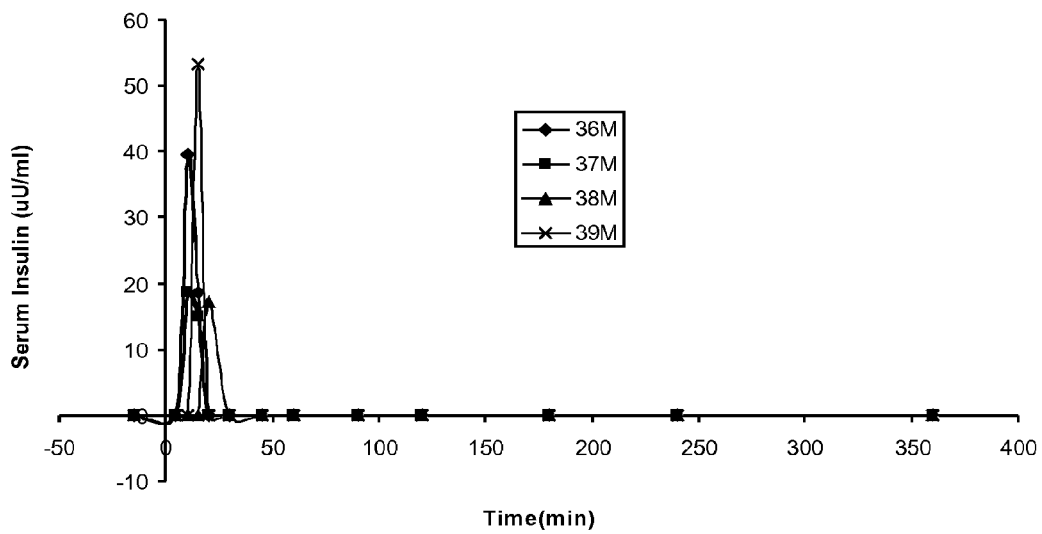
Figure 10:
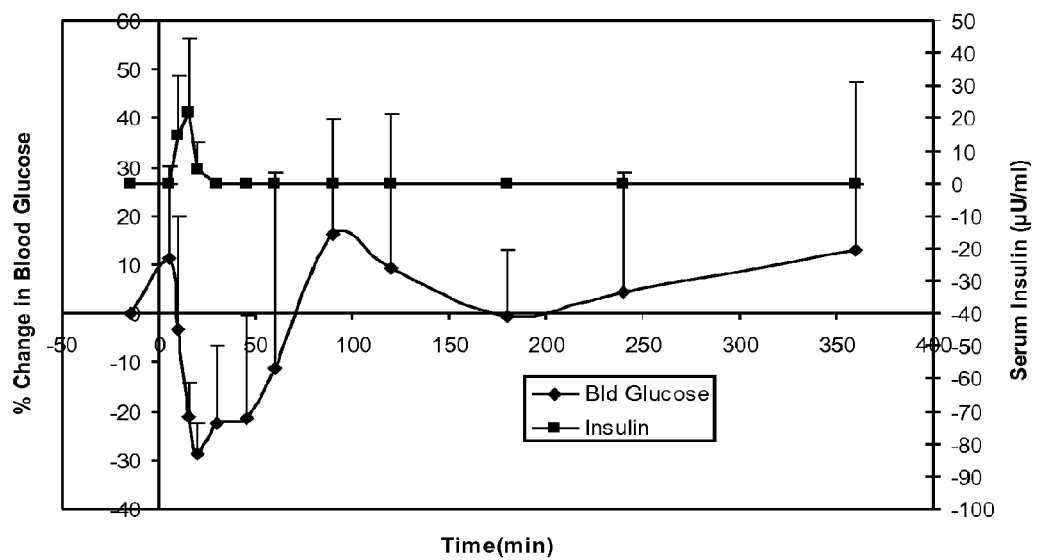

Four male primates were administered one tablet of Formulation 1 of Example 6. The results are shown in FIG. 5 (glucose reduction) and FIG. 6 (serum insulin concentrations). The averaged results are shown in FIG. 7. After a wash-out period, the same group of four primates were each administered Formulation 2 of Example 6. These results are shown in FIGS. 8-10.

Figure 11:
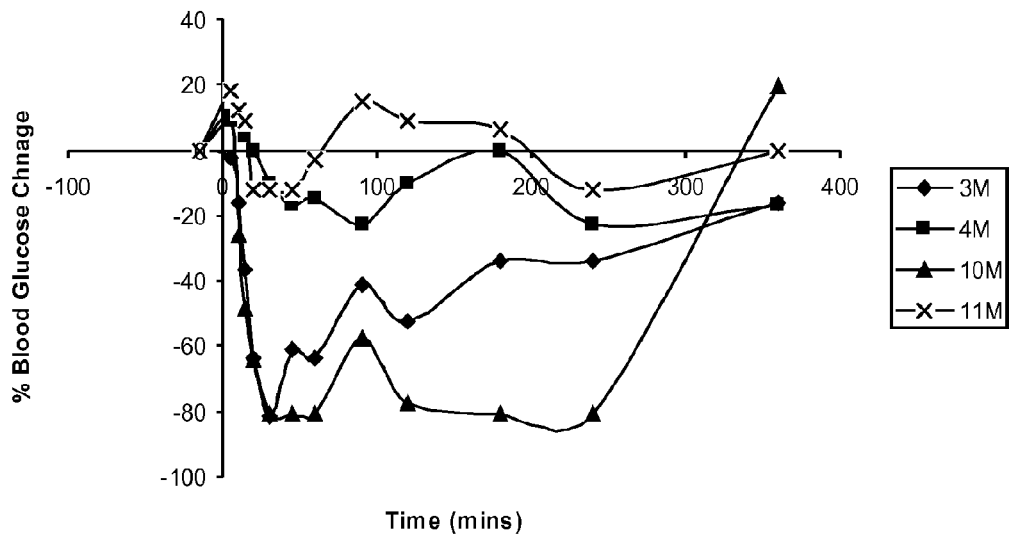
Figure 12:
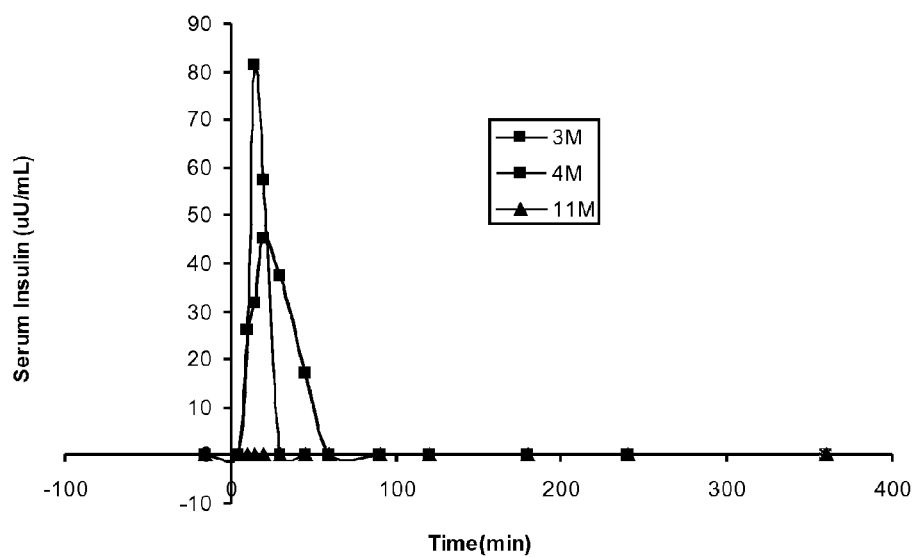

A different group of four male primates were each administered one tablet of Formulation 3 of Example 6. Glucose reduction is shown in FIG. 11. Serum insulin levels for 3 of the four monkeys are shown in FIG. 12.

Example 8

Preparation of Tablets Containing Co-Lyophilized Insulin/4-CNAB Powder

Tablets containing co-lypophilized insulin/sodium 4-CNAB powder and having the formulation shown in Table 6 were prepared as follows. First, insulin was dissolved in an aqueous solution containing sodium 4-CNAB and the solution was freeze dried according to the regimen in Table 4. The insulin/4-CNAB solution obtained from freeze-drying was then milled with a 35 mesh sieve and blended with copovidone and magnesium stearate (intragranular excipients). The composition was then dry granulated by roller compaction. Copovidone and magnesium stearate was added extragranularly and the granules were compressed into tablets at a pressure of about 1000 psi for 5 seconds.

Based on the process, tablets with the following amounts of ingredients were prepared:

TABLE 6

Insulin/4-CNAB (150 units/240 mg) Co-lyophilized Tablets

| Ingredients | Weight (mg/tablet) | Weight/Batch (g) |
|---|---|---|
| Insulin/4-CNAB (Co-lyophilized containing 150 Units of insulin) | 5.45/240 | 270.0 |
| Copovidone; NF/EP (intragranular) | 3.60 | 3.96 |
| Magnesium Stearate; NF/EP(intragranular) | 0.90 | 0.99 |
| Copovidone; NF/EP (extragranular) | 3.60 | 3.96 |
| Dibasic Calcium Phosphate Anhydrous, USP/EP | 103.75 | 114.13 |
| Magnesium Stearate | 2.70 | 2.97 |
| Theoretical Tablet Weight | 360 mg | |

Example 9

Preparation of Tablets Containing Co-Lyophilized Insulin/4-CNAB Powder

Tablets containing co-lyophilized insulin/4-CNAB and having the formulation shown in Table 7 were prepared by the procedure set forth in Example 8.

TABLE 7

Insulin/4-CNAB (150 units/400 mg) Co-lyophilized Tablets

| Ingredients | Weight (mg/tablet) | Weight/Batch (g) |
|---|---|---|
| *Insulin/4-CNAB (Co-lyophilized) (Containing 150 units of Insulin) | 5.45/400 | 430.588 |
| Copovidone; NF/EP (intragranular) | 5.80 | 6.160 |
| Magnesium Stearate; NF/EP (intragranular) | 1.40 | 1.487 |
| Copovidone; NF/EP (extragranular) | 5.75 | 6.106 |
| Dibasic Calcium Phosphate Anhydrous, USP/EP | 157.20 | 166.946 |
| Magnesium Stearate | 4.40 | 4.673 |
| Theoretical Tablet Weight | 580 mg | |

Example 10

Preparation of Tablets Containing Co-Dried Insulin/4-CNAB Powder Obtained from Rotary Evaporation Sodium 4-CNAB (935.7 g, 0.4 wt % water by Karl Fisher titration) and purified water (4850 mL) were charged to a 20 L, borosilicate, rotary evaporator flask. The flask was attached to a rotary evaporator and rotated at about 60 rpm until the solids dissolved. The rotation was stopped. The flask was removed from the rotary evaporator and insulin (64.1 g, 27.4 U/mg) was added. The flask was re-attached to the rotary evaporator and the insulin was allowed to dissolve without agitation. The water was removed rapidly with the rotary evaporator bath set at about 45 C and the internal pressure set at about 5 mm Hg. The walls of the rotary evaporator flask became coated with solid co-dried insulin/4CNAB as the water was removed. These solids were scraped from the walls of the flask and dried in a vacuum oven set at full vacuum and 50° C. until the water content was less than 10 wt % by Karl Fisher analysis. In most cases the vacuum drying time could be reduced by breaking up the larger lumps of co-dried material about midway through the vacuum oven drying cycle. The dried material was then hammer milled so that it would pass through a 35 mesh screen. The milled, powdery material was placed in a suitable container and stored in a freezer at −20° C. or lower until used. The recovery of co-dried material was about 95%.

The co-dried insulin/4-CNAB prepared as described above, was mixed with povidone and magnesium stearate in the amounts shown in Table 8 below and compressed into tablets tablets at a pressure of about 1000 psi for 5 seconds.

TABLE 8

| Ingredient | Amount |
|---|---|
| 4-CNAB Sodium Salt | 80 mg |
| Recombinant Human Insulin | 150 Units (27.4 U/mg) |
| Povidone, USP (Kollidon 90F) | 1 mg |
| Magnesium stearate, NF | 1 mg |

Example 11

Preparation of Capsules Containing Co-dried Insulin/4-CNAB Powder Obtained from Rotary Evaporation The process of example 10 was repeated to prepare the co-dried insulin/4-CNAB powder. 80 mg of sodium 4-CNAB/150 Units of insulin was placed, without excipients, into size 2 hard gelatin opaque white capsules.

Example 12

Preparation of Tablets Containing Co-dried Insulin/4-CNAB Powder Obtained from Rotary Evaporation The process of example 10 was repeated to prepare the co-dried insulin/4-CNAB powder, except that 966.7 g of 4-CNAB, 5000 mL of water and 33.23 g of insulin were charged to the rotary evaporator flask.

Tablets having the formulation shown in Table 9 were prepared by the procedure set forth in Example 10:

TABLE 9

| Ingredient | Amount |
|---|---|
| 4-CNAB Sodium Salt | 80 mg |
| Recombinant Human Insulin | 75 Units (27.4 U/mg) |
| Povidone, USP (Kollidon 90F) | 1 mg |
| Magnesium stearate, NF | 1 mg |

Example 13

Preparation of Capsules Containing Co-Dried Insulin/4-CNAB Powder Obtained from Rotary Evaporation The process of example 10 was repeated to prepare the co-dried insulin/4-CNAB powder, except that 966.7 g of 4-CNAB, 5000 mL of water and 33.23 g of insulin were charged to the rotary evaporator flask.

80 mg of sodium 4-CNAB/75 Units of insulin was placed, without excipients, into size 2 hard gelatin opaque white capsules.

Example 14

Preparation of Tablets Containing Co-Dried Insulin/4-CNAB Powder Obtained from Rotary Evaporation The process of Example 10 was repeated to prepare tablets, except that povidone and magnesium stearate were not included in the formulation.

Example 15

Preparation of Tablets Containing Co-Dried Insulin/4-CNAB Powder Obtained from Rotary Evaporation The process of Example 10 was repeated to prepare the co-dried insulin/4-CNAB powder, except that 241.7 g of 4-CNAB, 1260 mL of water and 8.3 g of insulin were charged to the rotary evaporator flask.

Tablets having the formulation shown in Table 10 were prepared by the procedure set forth in Example 10.

TABLE 10

| Ingredient | Amount |
| --- | --- |
| 4-CNAB Sodium Salt | 160 mg |
| Recombinant Human Insulin | 150 Units (27.4 U/mg) |
| Povidone, USP (Kollidon 90F) | 0 mg |
| Magnesium stearate, NF | 0 mg |

Example 16

Preparation of Tablets Containing Co-Dried Insulin/4-CNAB Powder Obtained from Rotary Evaporation The process of example 10 was repeated to prepare the co-dried insulin/4-CNAB powder, except that 245.8 g of 4-CNAB, 1280 mL of water and 4.3 g of insulin were charged to the rotary evaporator flask.

Tablets having the formulation shown in Table 11 were prepared by the procedure set forth in Example 10.

TABLE 11

| Ingredient | Amount |
| --- | --- |
| 4-CNAB Sodium Salt | 320 mg |
| Recombinant Human Insulin | 150 Units (27.4 U/mg) |
| Povidone, USP (Kollidon 90F) | 0 mg |
| Magnesium stearate, NF | 0 mg |

Example 17

Preparation of Tablets Containing Co-Dried Insulin/4-CNAB Powder Obtained from Rotary Evaporation The process of example 10 was repeated to prepare the co-dried insulin/4-CNAB powder, except that 245.4 g of 4-CNAB, 1280 mL of water and 5.6 g of insulin were charged to the rotary evaporator flask.

Tablets having the formulation shown in Table 12 were prepared by the procedure set forth in Example 10.

TABLE 12

| Ingredient | Amount |
| --- | --- |
| 4-CNAB Sodium Salt | 160 mg |
| Recombinant Human Insulin | 100 Units (27.4 U/mg) |
| Povidone, USP (Kollidon 90F) | 0 mg |
| Magnesium stearate, NF | 0 mg |

Example 18

Preparation of Tablets Containing Co-Dried Insulin/4-CNAB Powder Obtained from Rotary Evaporation The process of example 10 was repeated to prepare the co-dried insulin/4-CNAB powder, except that 247.2 g of 4-CNAB, 1300 mL of water and 2.8 g of insulin were charged to the rotary evaporator flask.

Tablets having the formulation shown in Table 13 were prepared by the procedure set forth in Example 10.

TABLE 13

| Ingredient | Amount |
| --- | --- |
| 4-CNAB Sodium Salt | 320 mg |
| Recombinant Human Insulin | 100 Units (27.4 U/mg) |
| Povidone, USP (Kollidon 90F) | 0 mg |
| Magnesium stearate, NF | 0 mg |

Example 19

Preparation of Tablets Containing Co-Dried Insulin/4-CNAB Powder Obtained from Rotary Evaporation The process of example 10 was repeated to prepare the co-dried insulin/4-CNAB powder, except that 247.2 g of 4-CNAB, 1300 mL of water and 2.8 g of insulin were charged to the rotary evaporator flask.

Tablets having the formulation shown in Table 14 were prepared by the procedure set forth in Example 10.

TABLE 14

| Ingredient | Amount |
| --- | --- |
| 4-CNAB Sodium Salt | 320 mg |
| Recombinant Human Insulin | 100 Units (27.4 U/mg) |

TABLE 14-continued

| Ingredient | Amount |
| --- | --- |
| Povidone, USP (Kollidon 90F) | 1 mg |
| Magnesium stearate, NF | 1 mg |

Example 20

Preparation of Tablets Containing Co-Dried Insulin/4-CNAB Powder Obtained from Rotary Evaporation The process of example 10 was repeated to prepare the co-dried insulin/4-CNAB powder, except that 245.8 g of 4-CNAB, 1280 mL of water and 4.3 g of insulin were charged to the rotary evaporator flask.

Tablets having the formulation shown in Table 15 were prepared by the procedure set forth in Example 10.

TABLE 15

| Ingredient | Amount |
| --- | --- |
| 4-CNAB Sodium Salt | 320 mg |
| Recombinant Human Insulin | 150 Units (27.4 U/mg) |
| Povidone, USP (Kollidon 90F) | 1 mg |
| Magnesium stearate, NF | 1 mg |

Example 21

Preparation of Tablets Based on Granulated Gelatin-Based Formulation

Tablets having the formulation shown in Table 16 were prepared as follows. Gelatin was milled using a KitchenAid™ coffee grinder and later screened through a sieve of size #35. Afterwards, the required amount of insulin was weighed and dispersed into purified water. The amount of purified water used was about 15% of the theoretical batch weight. For a theoretical batch size of 1200 tablets, 50 g of Insulin is dispersed in 46.7 g of purified water.

Sodium 4-CNAB and the milled gelatin were transferred into an appropriate sized high shear granulator and mixed for about 2 minutes. The sodium 4-CNAB and gelatin mixture was granulated first with the aqueous dispersion of insulin and later with purified water using a pump device. The resultant wet granules were evenly dispersed in oven trays and dried in a vacuum oven (Temperature=50° C.; Vacuum=5 mm Hg) for at least 8 hours. The dried granules were characterized based on moisture (0.5%) and insulin content and insulin content uniformity. The granules were milled and screened through a sieve of size 0.02 inches. Prior to tablet compression, dibasic calcium phosphate and magnesium stearate were blended with dry granules. Tablets were compressed using an EKO single punch station press.

Based on the above procedure, tablets containing the following amounts of ingredients were prepared.

TABLE 16

| Ingredients | Weight (mg/dose) |
| --- | --- |
| Recombinant Human Insulin | 5.45 |
| 4-CNAB Monosodium salt | 240 |
| Gelatin (Type A) | 12 |
| Dibasic Calcium Phosphate (extragranular) | 113.80 |
| Magnesium Stearate (extragranular) | 3.75 |
| Total Weight (mg/tablet) | 375 |

The tablets prepared by this process had an average weight of about 373.5 mg, a thickness of 5 mm and an average hardness of about 10.3 kP.

Example 22

Preparation of Granulated Tablets (Wet Granulation)

Tablets having the formulation shown in Tables 17 and 18 were prepared as follows.

TABLE 17

Drug Product Components: Insulin/4-CNAB (150 Units/80 mg) Tablets

| Component | Function |
| --- | --- |
| 4-CNAB Sodium Salt | Delivery Agent |
| Recombinant Human Insulin | Drug (Active Agent) |
| Povidone, USP (Kollidon 90F) | Binder |
| Dibasic Calcium Phosphate, Anhydrous, USP | Binder |
| Magnesium stearate, NF | Lubricant |
| Purified Water, USP | Granulating fluid |

Sodium 4-CNAB was milled using a Quadro Comil equipped with a 35 mesh screen. Insulin and the milled sodium 4-CNAB were blended together, and transferred to a Key Instruments KG 5 high shear granulator equipped with a 5 Liter bowl. The material was granulated with povidone. Once the addition of the povidone was completed, the container was rinsed with small portions of purified water and added to the granulation until the desired granulation was achieved.

The granulation was transferred to clean stainless steel trays and dried in a vacuum oven at 50° C. until the moisture content was less than 5.0% w/w and then milled through a 35 mesh screen and further dried until the moisture content less than 1.5% w/w. The granulation was assayed for insulin and sodium 4-CNAB using a validated HPLC method. The insulin assay of the granulation was used for calculating the required quantity of Emcompress for the batch. The required amount of Emcompress was added to the granulation and blending was performed in a V-blender for 15 minutes. Samples were collected for bend uniformity testing. After acceptable blend uniformity data was obtained the required amount of magnesium stearate was added and blending was performed for 3 minutes. The resulting blend was compressed into tablets using a Korsch EKO single station tablet press. The target tablet weight was 125 mg with a range of 119-131 mg, acceptable tablet hardness range was 5-11 kP with a target tablet hardness of 7.0 kP. The tablets exhibited an average thickness of 7.8 mm. The Insulin/4-CNAB (150 Units/80 mg) tablets were packaged in a container closure system consisting of a 60 cc HDPE Round, White bottle with 33 mm Child Resistant Cap 1 with Safe-Gard® 75 m Induction Innerseal and Cotton Coil 12 gm/yd.

Based on this procedure, the following amounts of ingredients were used to prepare the tablets:

TABLE 18

Drug Product Composition: Insulin/4-CNAB (150 Units/80 mg) Tablets (Batch Size 6,200 Tablets)

| Component | mg/Tablet | Batch Formula (g) |
|---|---|---|
| 4-CNAB Sodium Salt | 76-84 | 496.0 |
| Recombinant Human Insulin | 5.32-5.88 (142.5-157.5 Units) | 35.1 |
| Povidone USP (Kollidon 90F) | 0.38-0.42 | 2.2 |
| Dibasic Calcium Phosphate, Anhydrous, USP | 35.9-39.7 | 195.2 |
| Magnesium Stearate, NF Impalpable Powder | 1.14-1.26 | 6.7 |
| Total Weight (mg) | 118.8-131.3 | 735.2 |

Example 23

Human Clinical Study of Orally Administered Insulin

Six healthy male subjects between the ages of 18 and 40 were orally administered one tablet or capsule, depending on the treatment period indicated below after an 8-hour fast the previous night. Glucose and insulin values were obtained from blood samples fifteen minutes prior to dosing (t=0) and 5, 10, 15, 20, 25, 30, 35, 40, 45, 50, 60, 90 and 120 minutes after dosing. After receiving the first tablet or capsule, the subject underwent at least a 72 hour washout period before receiving the next tablet or capsule.

The administration regimen was as follows:

TABLE 19

| Treatment Period | Summary of Dosage | Preparation Details |
|---|---|---|
| A | Wet granulation tablet | Example 22 |
| B | Rotary evaporation tablet | Example 10 |
| C | Rotary evaporation capsule | Example 11 |
| D | Rotary evaporation tablet | Example 12 |
| E | Rotary evaporation capsule | Example 13 |

Results for the treatment regiment are set forth below:

TABLE 20

Insulin Mean PK Results obtained from Individual Baseline-adjusted Insulin Concentrations

| Treatment | | Cmax (µU/mL) | Tmax (min) | AUClast (µU/mL * min) | New/Reference Cmax ratio | New/Reference AUC ratio |
|---|---|---|---|---|---|---|
| A | N | 6 | 6 | 6 | N/A | N/A |
| | Mean | 15.250 | 19.167 | 346.250 | | |
| | SD | 10.064 | 2.041 | 227.404 | | |
| | Min | 4.50 | 15.00 | 40.00 | | |
| | Max | 31.00 | 20.00 | 700.00 | | |
| | CV % | 66.0 | 10.6 | 65.7 | | |
| B | N | 6 | 6 | 6 | 1.8 | 1.2 |
| | Mean | 27.500 | 19.167 | 422.708 | | |
| | SD | 9.925 | 10.685 | 256.758 | | |
| | Min | 14.50 | 10.00 | 133.75 | | |
| | Max | 41.50 | 40.00 | 860.00 | | |
| | CV % | 36.1 | 55.7 | 60.7 | | |
| C | N | 5 | 5 | 5 | | |
| | Mean | 8.800 | 35.000 | 260.000 | | |
| | SD | 7.497 | 33.727 | 313.358 | | |
| | Min | 0.50 | 10.00 | 11.25 | | |
| | Max | 21.00 | 90.00 | 805.00 | | |
| | CV % | 85.2 | 96.4 | 120.5 | | |
| C (without outlier-Subject 4, 90 min timepoint) | N | 5 | 5 | 5 | 0.2 | 0.4 |
| | Mean | 5.200 | 41.000 | 128.000 | | |
| | SD | 3.347 | 46.287 | 73.912 | | |
| | Min | 0.50 | 10.00 | 11.25 | | |
| | Max | 8.50 | 120.00 | 200.00 | | |
| | CV % | 64.4 | 112.9 | 57.7 | | |
| D | N | 6 | 6 | 6 | 0.3 | 0.3 |
| | Mean | 9.333 | 10.000 | 110.000 | | |
| | SD | 4.215 | 3.162 | 59.713 | | |
| | Min | 1.00 | 5.00 | 7.50 | | |
| | Max | 12.50 | 15.00 | 172.50 | | |
| | CV % | 45.2 | 31.6 | 54.3 | | |
| E | N | 5 | 4 | 5 | 0.4 | 0.4 |
| | Mean | 5.600 | 38.750 | 140.500 | | |
| | SD | 6.004 | 37.053 | 123.392 | | |
| | Min | 0.00 | 5.00 | 0.00 | | |
| | Max | 15.50 | 90.00 | 273.75 | | |
| | CV % | 107.2 | 95.6 | 87.8 | | |

TABLE 21

Insulin Mean PK Results obtained from Individual Insulin Concentrations

| Treatment | | Cmax (µU/mL) | Tmax (min) | AUClast (µU/mL * min) | New/Reference Cmax ratio | New/Reference AUC ratio |
|---|---|---|---|---|---|---|
| A | N | 6 | 6 | 6 | N/A | N/A |
| | Mean | 30.333 | 19.167 | 1882.917 | | |
| | SD | 11.343 | 2.041 | 435.067 | | |
| | Min | 16.00 | 15.00 | 1107.50 | | |
| | Max | 44.00 | 20.00 | 2222.50 | | |
| | CV % | 37.4 | 10.6 | 23.1 | | |
| B | N | 6 | 6 | 6 | 1.6 | 1.2 |
| | Mean | 47.167 | 19.167 | 2286.250 | | |
| | SD | 14.148 | 10.685 | 1117.921 | | |
| | Min | 21.00 | 10.00 | 747.50 | | |
| | Max | 59.00 | 40.00 | 4222.50 | | |
| | CV % | 30.0 | 55.7 | 48.9 | | |
| C (*) | N | 6 | 6 | 6 | 0.6 | 0.8 |
| | Mean | 18.667 | 27.500 | 1562.083 | | |
| | SD | 4.179 | 45.689 | 247.454 | | |
| | Min | 12.00 | 0.00 | 1127.50 | | |
| | Max | 24.00 | 120.00 | 1777.50 | | |
| | CV % | 22.4 | 166.1 | 15.8 | | |
| D | N | 6 | 6 | 6 | 0.8 | 0.9 |
| | Mean | 24.500 | 10.000 | 1640.417 | | |
| | SD | 6.863 | 3.162 | 522.110 | | |
| | Min | 18.00 | 5.00 | 867.50 | | |
| | Max | 36.00 | 15.00 | 2500.00 | | |
| | CV % | 28.0 | 31.6 | 31.8 | | |
| E | N | 6 | 6 | 6 | 0.9 | 0.9 |
| | Mean | 26.167 | 26.667 | 1744.167 | | |
| | SD | 15.052 | 34.303 | 414.203 | | |
| | Min | 16.00 | 0.00 | 1102.50 | | |
| | Max | 54.00 | 90.00 | 2222.50 | | |
| | CV % | 57.5 | 128.6 | 23.7 | | |

(*) Insulin concentration Measured at 90 min in Subject 4 was considered an outlier hence not included in the PK analysis.

Model-independent pharmacokinetic metrics were calculated using WinNonlin (v 4.5, Scientific Consulting, Inc.) from individual plasma concentration data. This program analyzes data using the standard methods described by Gibaldi and Perrier. The area under the plasma concentration-time curve (AUC) was estimated by the linear trapezoidal rule.

"Baseline" is defined as average plasma insulin concentrations as assessed prior to study drug administration (i.e. −15 and 0 minute samples averaged). Adjusted concentrations were obtained by subtracting the individual baseline from each individual time point (Ct—Co). Negative values were not included in the data analysis.

Figure 13:
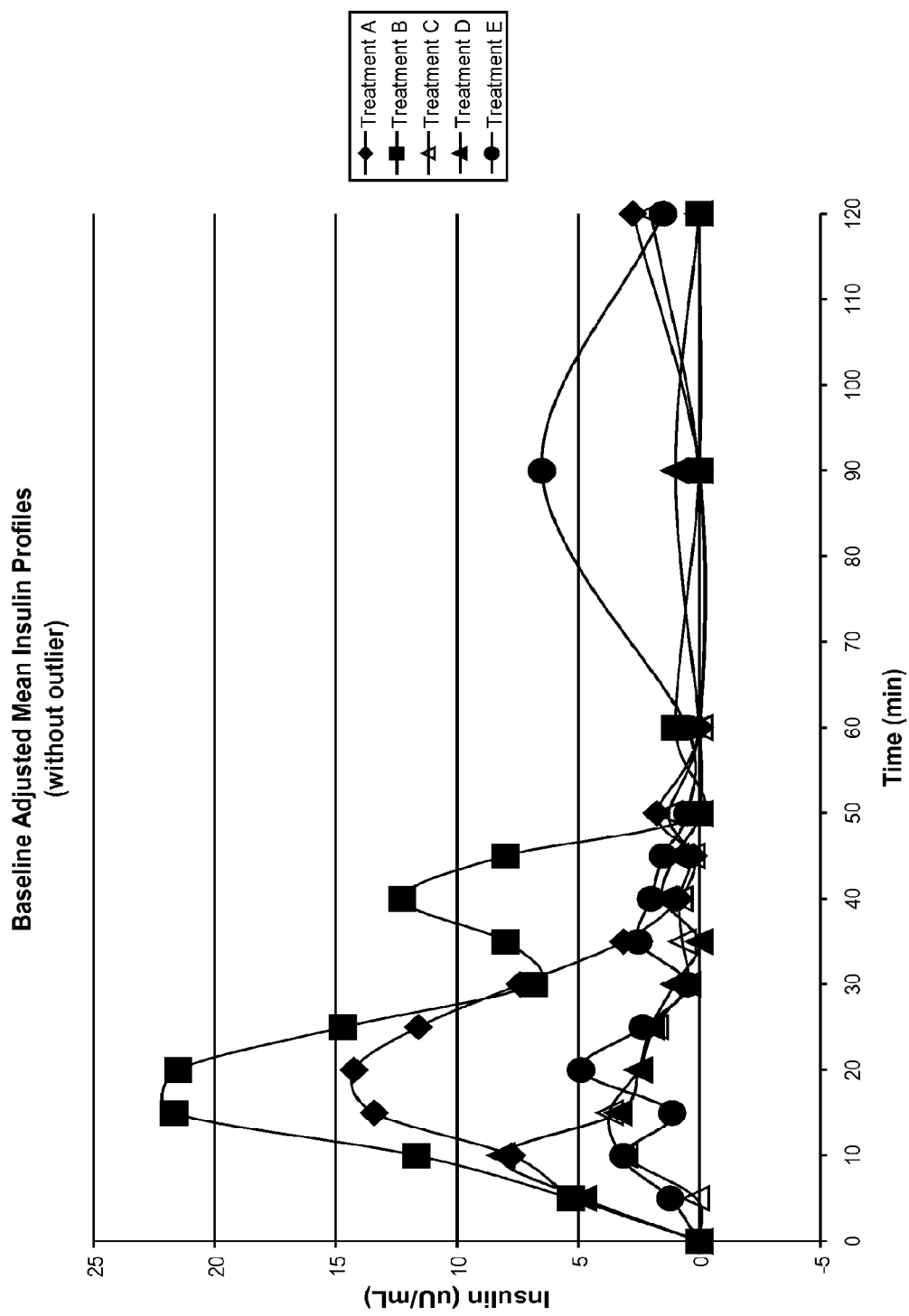
FIGS. 13 and 14 set forth the results of insulin dosage forms administered to humans as described in Example 23.
Figure 14:
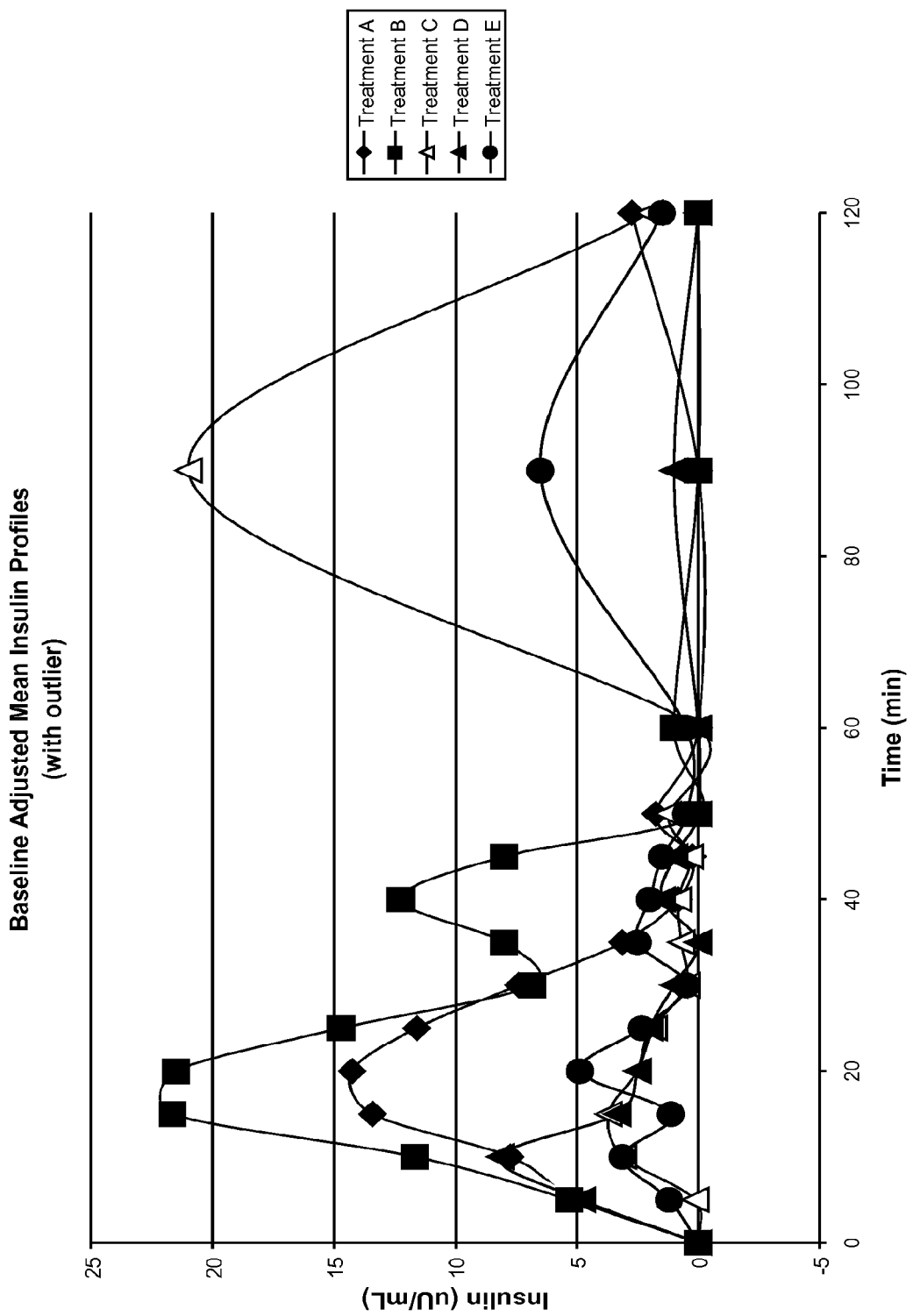

Results for the adjusted-mean insulin profiles are shown in FIGS. 13 (without outlier) and 14 (with outlier).

Example 24

Human Clinical Study of Orally Administered Insulin

The protocol used in Example 23 was used for the following treatment regimens:

TABLE 22

| Treatment Period | Summary of Dosage | Preparation Details |
|---|---|---|
| A | Rotary Evaporation Tablets | Example 10 |
| B | Rotary Evaporation Tablets | Example 14 |
| C | Rotary Evaporation Tablets | Example 15 |
| D | Rotary Evaporation Tablets | Example 16 |
| E | Rotary Evaporation Tablets | Example 17 |
| F | Rotary Evaporation Tablets | Example 18 |

Results for the treatment regiment are set forth below:

TABLE 23

Insulin Mean PK Results obtained from Individual Baseline-adjusted Insulin Concentrations

| Treatment | | Cmax (µU/mL) | Tmax (min) | AUClast (µU/mL * min) |
|---|---|---|---|---|
| A | N | 6 | 6 | 6 |
| | Mean | 30.633 | 17.500 | 795.615 |
| | SD | 20.977 | 5.244 | 542.094 |
| | Min | 10.86 | 10.00 | 331.76 |
| | Max | 66.62 | 25.00 | 1742.30 |
| | CV % | 68.5 | 30.0 | 68.1 |
| B | N | 6 | 6 | 6 |
| | Mean | 22.441 | 13.333 | 312.535 |
| | SD | 16.489 | 2.582 | 214.398 |
| | Min | 8.00 | 10.00 | 118.83 |
| | Max | 52.00 | 15.00 | 649.80 |
| | CV % | 73.5 | 19.4 | 68.6 |
| C | N | 6 | 6 | 6 |
| | Mean | 28.546 | 21.667 | 741.708 |
| | SD | 23.848 | 14.024 | 737.074 |
| | Min | 6.05 | 5.00 | 100.93 |
| | Max | 69.20 | 45.00 | 1787.75 |
| | CV % | 83.5 | 64.7 | 99.4 |
| D | N | 6 | 6 | 6 |
| | Mean | 29.421 | 16.667 | 575.435 |
| | SD | 17.155 | 4.082 | 384.295 |
| | Min | 13.56 | 10.00 | 176.14 |
| | Max | 53.08 | 20.00 | 1210.13 |
| | CV % | 58.3 | 24.5 | 66.8 |

TABLE 23-continued

Insulin Mean PK Results obtained from Individual Baseline-adjusted Insulin Concentrations

| Treatment | | Cmax (μU/mL) | Tmax (min) | AUClast (μU/mL * min) |
|---|---|---|---|---|
| E | N | 6 | 6 | 6 |
|   | Mean | 18.556 | 15.833 | 303.702 |
|   | SD | 14.849 | 2.041 | 304.338 |
|   | Min | 1.49 | 15.00 | 13.35 |
|   | Max | 39.25 | 20.00 | 799.38 |
|   | CV % | 80.0 | 12.9 | 100.2 |
| F | N | 6 | 6 | 6 |
|   | Mean | 20.971 | 19.167 | 536.952 |
|   | SD | 16.710 | 9.704 | 528.919 |
|   | Min | 2.14 | 5.00 | 15.06 |
|   | Max | 44.11 | 30.00 | 1312.61 |
|   | CV % | 79.7 | 50.6 | 98.5 |

TABLE 24

Insulin Mean PK Results obtained from Individual Insulin Concentrations

| Treatment | | Cmax (μU/mL) | Tmax (min) | AUClast (μU/mL * min) |
|---|---|---|---|---|
| A | N | 6 | 6 | 6 |
|   | Mean | 41.945 | 17.500 | 1905.513 |
|   | SD | 23.681 | 5.244 | 880.650 |
|   | Min | 14.94 | 10.00 | 794.20 |
|   | Max | 81.36 | 25.00 | 3251.53 |
|   | CV % | 56.5 | 30.0 | 46.2 |
| B | N | 6 | 6 | 6 |
|   | Mean | 35.740 | 13.333 | 1590.567 |
|   | SD | 14.956 | 2.582 | 246.447 |
|   | Min | 20.30 | 10.00 | 1199.00 |
|   | Max | 63.19 | 15.00 | 1961.45 |
|   | CV % | 41.8 | 19.4 | 15.5 |
| C | N | 6 | 6 | 6 |
|   | Mean | 40.807 | 21.667 | 1955.696 |
|   | SD | 24.954 | 14.024 | 896.595 |
|   | Min | 15.60 | 5.00 | 1032.25 |
|   | Max | 84.17 | 45.00 | 3295.53 |
|   | CV % | 61.2 | 64.7 | 45.8 |
| D | N | 6 | 6 | 6 |
|   | Mean | 42.480 | 16.667 | 1919.300 |
|   | SD | 18.411 | 4.082 | 493.982 |
|   | Min | 26.08 | 10.00 | 1363.75 |
|   | Max | 68.64 | 20.00 | 2586.25 |
|   | CV % | 43.3 | 24.5 | 25.7 |
| E | N | 6 | 6 | 6 |
|   | Mean | 31.770 | 15.833 | 1563.100 |
|   | SD | 13.306 | 2.041 | 334.769 |
|   | Min | 13.95 | 15.00 | 1030.88 |
|   | Max | 49.90 | 20.00 | 1984.25 |
|   | CV % | 41.9 | 12.9 | 21.4 |
| F | N | 6 | 6 | 6 |
|   | Mean | 33.737 | 19.167 | 1861.629 |
|   | SD | 16.049 | 9.704 | 654.066 |
|   | Min | 17.02 | 5.00 | 1271.05 |
|   | Max | 53.39 | 30.00 | 2969.95 |
|   | CV % | 47.6 | 50.6 | 35.1 |

Figure 15:
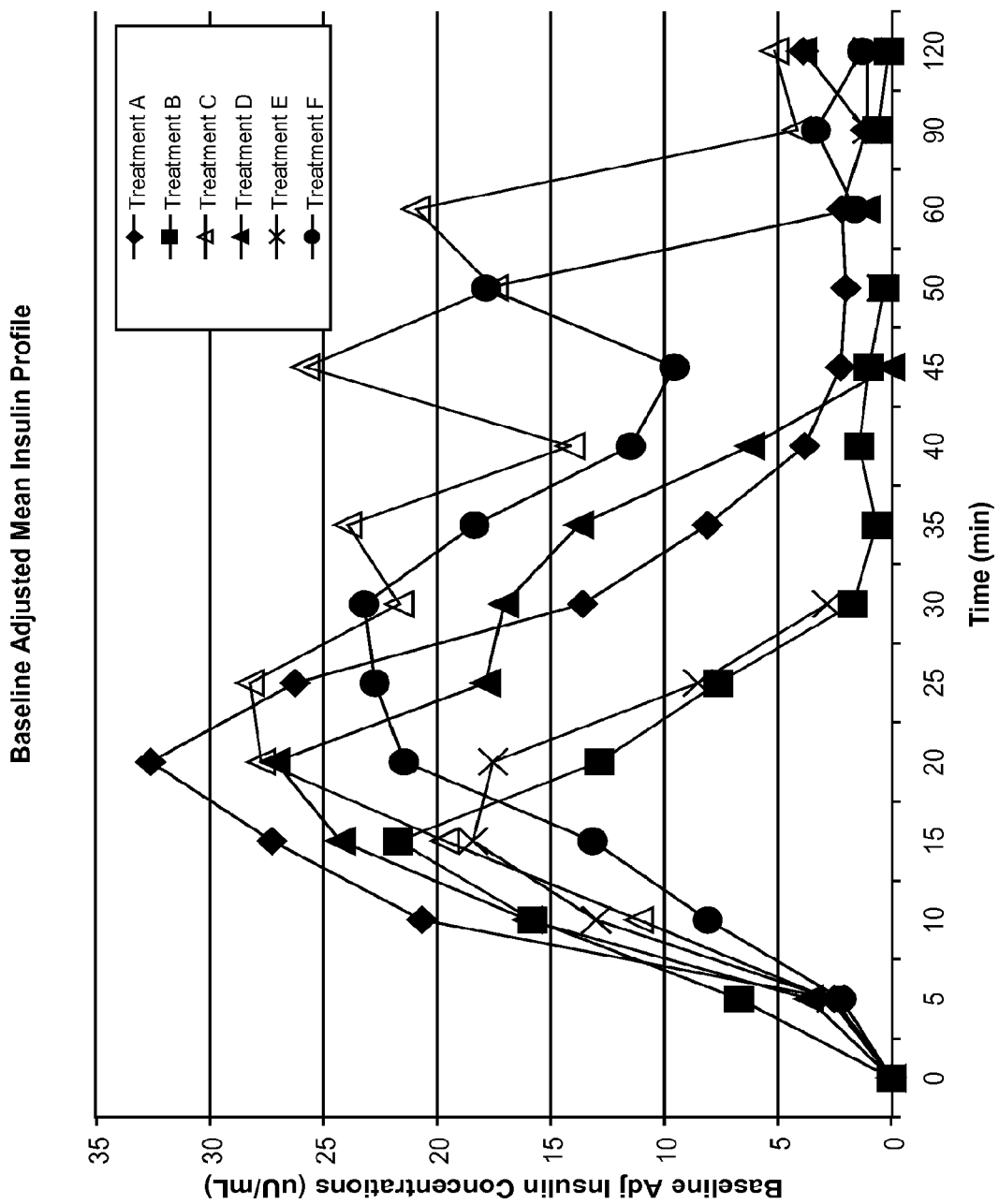
FIG. 15 sets forth the results of insulin dosage forms administered to humans as described in Example 24.

Results based on the adjusted mean insulin profiles are set forth in FIG. 15

Example 25

Human Clinical Study of Orally Administered Insulin

The protocol used in Example 23 was used for the following treatment regimens:

TABLE 25

| Treatment Period | Summary of Dosage | Preparation Details |
|---|---|---|
| A | Gelatin-Based Tablet | Example 21 |
| B | Co-lyophilized Tablets | Example 8 |
| C | Rotary Evaporation Tablets | Example 19 |
| D | Rotary Evaporation Tablets | Example 20 |
| E | Wet granulation Tablets | Example 22 |
| F | Co-lyophilized Tablets | Example 9 |

Results for the treatment regiment are set forth below:

TABLE 26

Insulin Mean PK Results obtained from Individual Baseline-adjusted Insulin Concentrations

| Treatment | | Cmax (μU/mL) | Tmax (min) | AUClast (μU/mL * min) | New/Reference Cmax ratio | New/Reference AUC ratio |
|---|---|---|---|---|---|---|
| A | N | 6 | 6 | 6 | 2.6 | 3.6 |
|   | Mean | 30.633 | 17.500 | 764.871 | | |
|   | SD | 20.977 | 5.244 | 508.089 | | |
|   | Min | 10.86 | 10.00 | 331.76 | | |
|   | Max | 66.62 | 25.00 | 1629.01 | | |
|   | CV % | 68.5 | 30.0 | 66.4 | | |
| B | N | 6 | 6 | 6 | 0.9 | 1.3 |
|   | Mean | 10.531 | 32.500 | 286.569 | | |
|   | SD | 12.685 | 43.215 | 284.348 | | |
|   | Min | 1.33 | 10.00 | 12.68 | | |
|   | Max | 33.61 | 120.00 | 731.20 | | |
|   | CV % | 120.5 | 133.0 | 99.2 | | |
| C | N | 6 | 6 | 6 | 1.0 | 1.2 |
|   | Mean | 12.203 | 15.000 | 254.679 | | |
|   | SD | 11.976 | 3.162 | 256.555 | | |
|   | Min | 4.89 | 10.00 | 50.65 | | |
|   | Max | 36.15 | 20.00 | 755.21 | | |
|   | CV % | 98.1 | 21.1 | 100.7 | | |
| D | N | 6 | 6 | 6 | 1.6 | 1.9 |
|   | Mean | 19.013 | 13.333 | 415.721 | | |
|   | SD | 24.735 | 6.055 | 601.162 | | |

TABLE 26-continued

Insulin Mean PK Results obtained from Individual Baseline-adjusted Insulin Concentrations

| Treatment | | Cmax (µU/mL) | Tmax (min) | AUClast (µU/mL * min) | New/Reference Cmax ratio | New/Reference AUC ratio |
|---|---|---|---|---|---|---|
|  | Min | 2.12 | 5.00 | 9.80 | | |
|  | Max | 67.82 | 20.00 | 1576.64 | | |
|  | CV % | 130.1 | 45.4 | 144.6 | | |
| E | N | 6 | 6 | 6 | N/A | N/A |
|  | Mean | 11.693 | 17.500 | 213.752 | | |
|  | SD | 10.033 | 8.216 | 180.716 | | |
|  | Min | 0.69 | 10.00 | 1.73 | | |
|  | Max | 26.70 | 30.00 | 415.56 | | |
|  | CV % | 85.8 | 46.9 | 84.5 | | |
| F | N | 6 | 6 | 6 | 0.8 | 0.7 |
|  | Mean | 9.092 | 15.000 | 142.221 | | |
|  | SD | 5.539 | 8.367 | 77.332 | | |
|  | Min | 1.83 | 10.00 | 4.56 | | |
|  | Max | 18.54 | 30.00 | 232.71 | | |
|  | CV % | 60.9 | 55.8 | 54.4 | | |

TABLE 27

Insulin Mean PK Results obtained from Individual Insulin Concentrations

| Treatment | | Cmax (µU/mL) | Tmax (min) | AUClast (µU/mL * min) | New/Reference Cmax ratio | New/Reference AUC ratio |
|---|---|---|---|---|---|---|
| A | N | 6 | 6 | 6 | 1.4 | 1.6 |
|  | Mean | 32.098 | 36.667 | 1966.079 | | |
|  | SD | 13.956 | 40.947 | 963.466 | | |
|  | Min | 9.85 | 15.00 | 800.78 | | |
|  | Max | 47.49 | 120.00 | 3345.18 | | |
|  | CV % | 43.5 | 111.7 | 49.0 | | |
| B | N | 6 | 6 | 6 | 1.0 | 1.1 |
|  | Mean | 21.730 | 32.500 | 1379.888 | | |
|  | SD | 10.133 | 43.215 | 281.651 | | |
|  | Min | 14.06 | 10.00 | 1151.90 | | |
|  | Max | 38.54 | 120.00 | 1922.78 | | |
|  | CV % | 46.6 | 133.0 | 20.4 | | |
| C | N | 6 | 6 | 6 | 1.1 | 1.2 |
|  | Mean | 23.873 | 15.000 | 1437.488 | | |
|  | SD | 12.681 | 3.162 | 401.442 | | |
|  | Min | 12.92 | 10.00 | 927.30 | | |
|  | Max | 48.83 | 20.00 | 2129.28 | | |
|  | CV % | 53.1 | 21.1 | 27.9 | | |
| D | N | 6 | 6 | 6 | 1.3 | 1.2 |
|  | Mean | 29.630 | 13.333 | 1492.971 | | |
|  | SD | 25.993 | 6.055 | 895.031 | | |
|  | Min | 7.20 | 5.00 | 398.93 | | |
|  | Max | 78.99 | 20.00 | 2857.18 | | |
|  | CV % | 87.7 | 45.4 | 59.9 | | |
| E | N | 6 | 6 | 6 | N/A | N/A |
|  | Mean | 22.507 | 17.500 | 1239.967 | | |
|  | SD | 8.105 | 8.216 | 244.282 | | |
|  | Min | 14.67 | 10.00 | 878.80 | | |
|  | Max | 32.70 | 30.00 | 1507.50 | | |
|  | CV % | 36.0 | 46.9 | 19.7 | | |
| F | N | 6 | 6 | 6 | 0.8 | 0.8 |
|  | Mean | 18.093 | 15.000 | 1030.767 | | |
|  | SD | 6.660 | 8.367 | 287.163 | | |
|  | Min | 11.84 | 10.00 | 648.45 | | |
|  | Max | 29.57 | 30.00 | 1360.88 | | |
|  | CV % | 36.8 | 55.8 | 27.9 | | |

Figure 16:
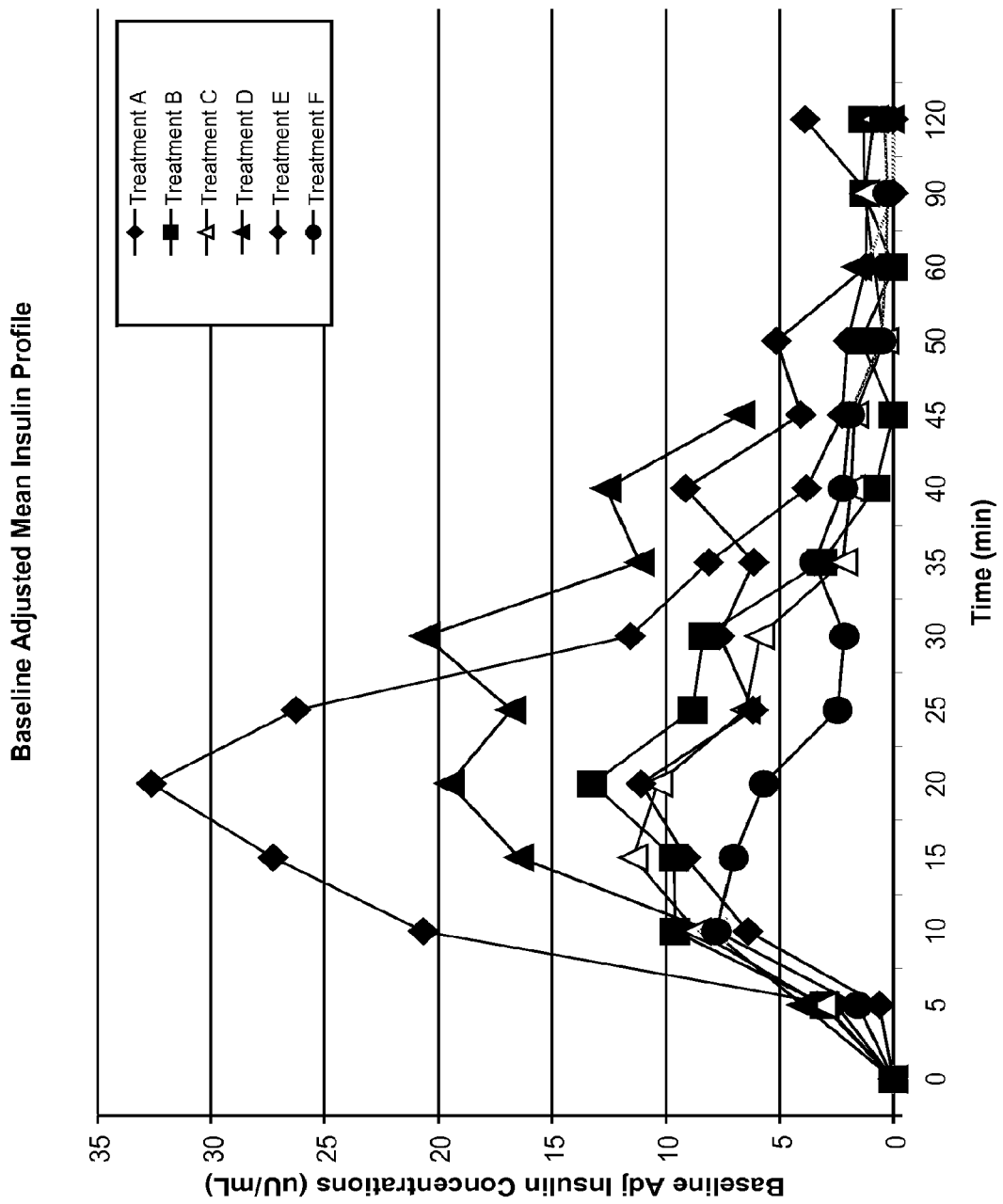
FIG. 16 sets forth the results of insulin dosage forms administered to humans as described in Example 25.

Results based on the adjusted mean insulin profiles are set forth in FIG. 16

Example 26

Human Clinical Study of Orally Administered Insulin 145 humans patients having type 2 diabetes who were failing metformin monotherapy were enrolled in a 90 day randomized double-blind placebo-controlled study. The patients remained on their metformin regimen, which varied from 125 mg-3000 mg per day individualized for each patient. 141 patients completed the study.

The patients were separated into 4 treatment groups as follows:

| Group | Insulin Dose | Dosing Regimen |
|---|---|---|
| 1 (n = 35) | Tablet of Example 22 (150 IU of insulin each) | 2 insulin tablets, 4 times daily |
| 2 (n = 35) | Tablet of Example 22 (150 IU of insulin) | 2 insulin tablets, 2 times daily 2 placebo tablets, 2 times daily |
| 3 (n = 36) | Tablet of Example 22 (150 IU of insulin) | 1 insulin tablet + 1 placebo tablet, 4 times daily |
| 4 (n = 35) | Placebo | 2 placebo tablets, 4 times daily |

Hemoglobin Alc counts were obtained about three weeks prior to beginning the study (screening) and just prior to the first administration of the oral insulin (t=0) or (baseline).

Figure 17:
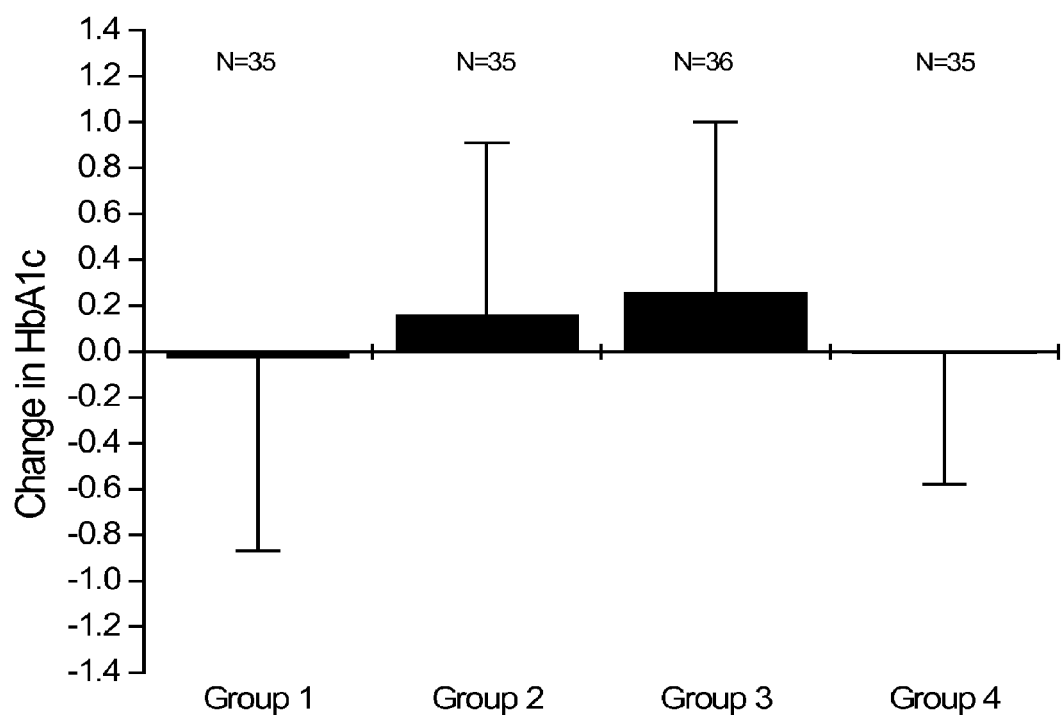
FIGS. 17-24 sets forth the results of insulin dosage forms administered to humans as described in Example 26.

Changes in HbA1c levels at the conclusion of the 90 day study for the four groups (relative to baseline) are shown in FIG. 17.

Figure 18:
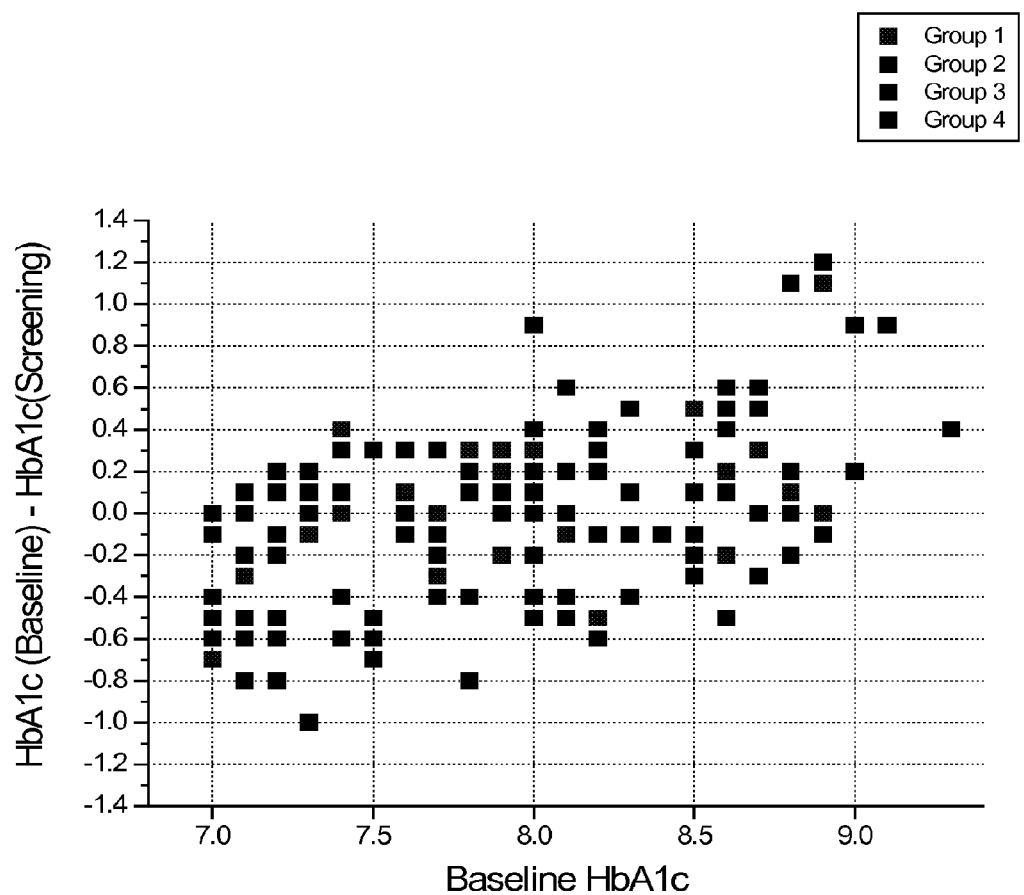
Figure 19:
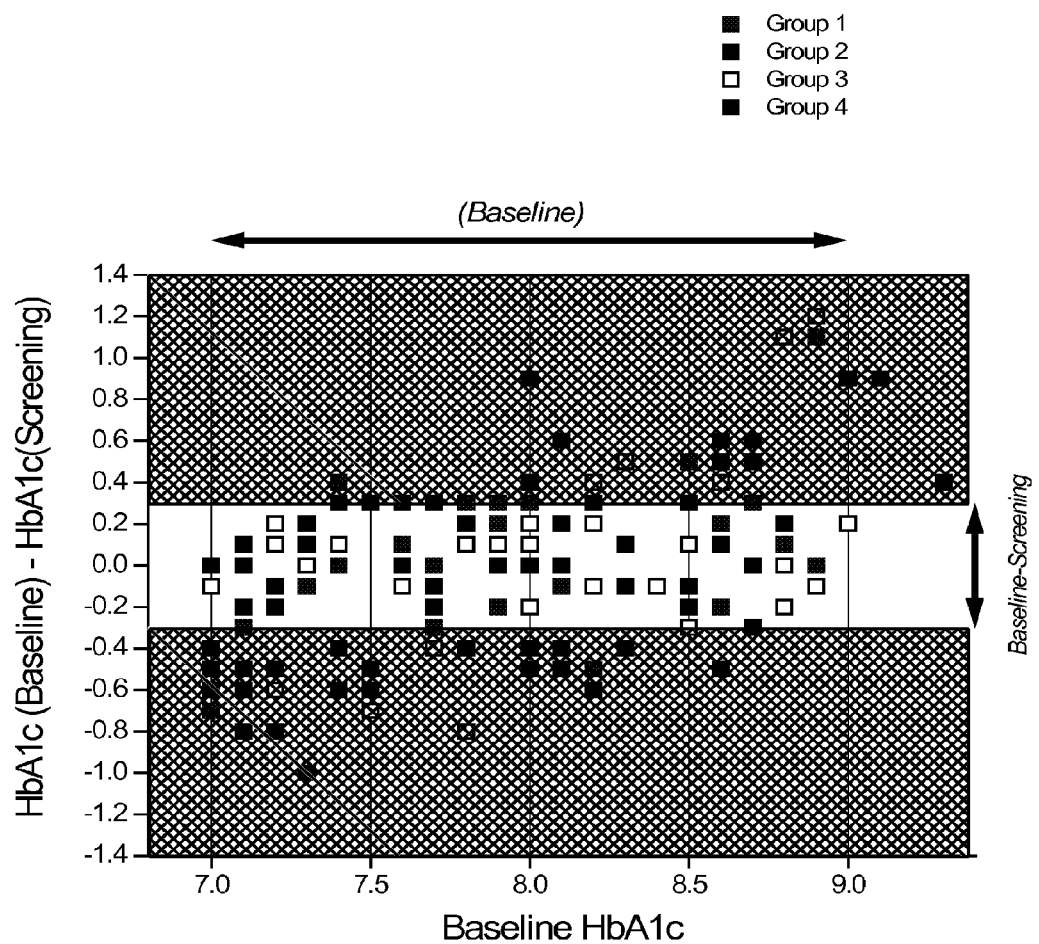

FIGS. 18 and 19 shows the difference between Hemoglobin Alc level at screening and at baseline for each of the subjects.

Figure 20:
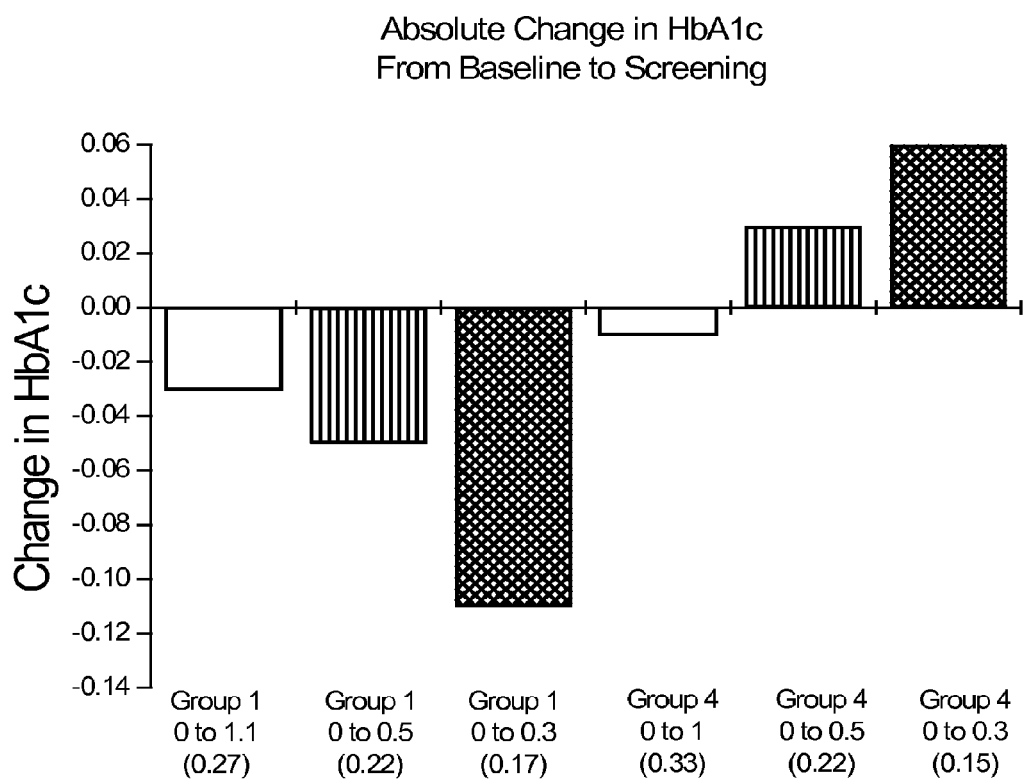

FIG. 20 is a bar graph of the changes in HbA1c level at 90 days compared to baseline for populations in groups 1 and 4 having a difference in HbA1c levels between screening and baseline of, for Group 1, 0-1.1, 0-0.5 and 0-0.3 and, for Group 4, 0-1, 0-0.5 and 0-0.3.

Figure 21:
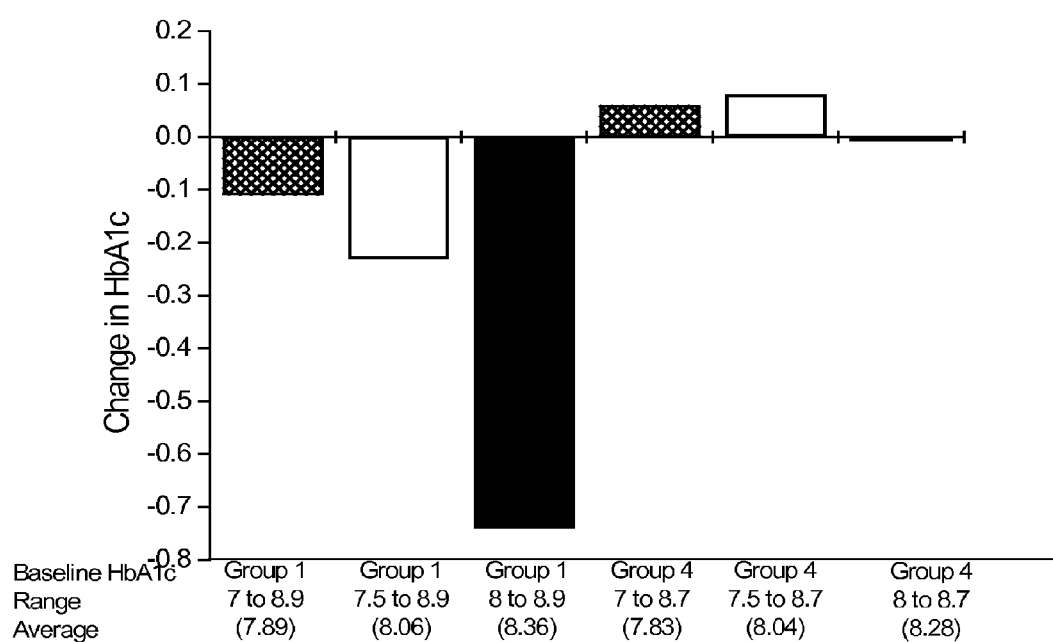

FIG. 21 is a bar graph of the change in HbA1c values after 90 days (compared to baseline) for patients in groups 1 and 4 having particular baseline HbA1c values and a difference in the HbA1c values from screening to baseline of 0-0.3. The first bar represents absolute changes in HbA1c levels (t=0 vs. t=90) for those subjects in Group I having baseline HbA1c levels ranging from 7 to 8.9 and a 0-0.3 variation of HbA1c levels between screening and at baseline. The second bar represents absolute changes in HbA1c levels for a subpopulation of Group 1 having baseline HbA1c levels of 7.5 to 8.9 and a 0-0.3 variation of HbA1c levels between screening and at baseline. The third bar represents a still narrower subpopulation—those patients of Group I having baseline HbA1c levels of 8 to 8.9 and a 0-0.3 variation of HbA1c levels between screening and at baseline.

Figure 22:
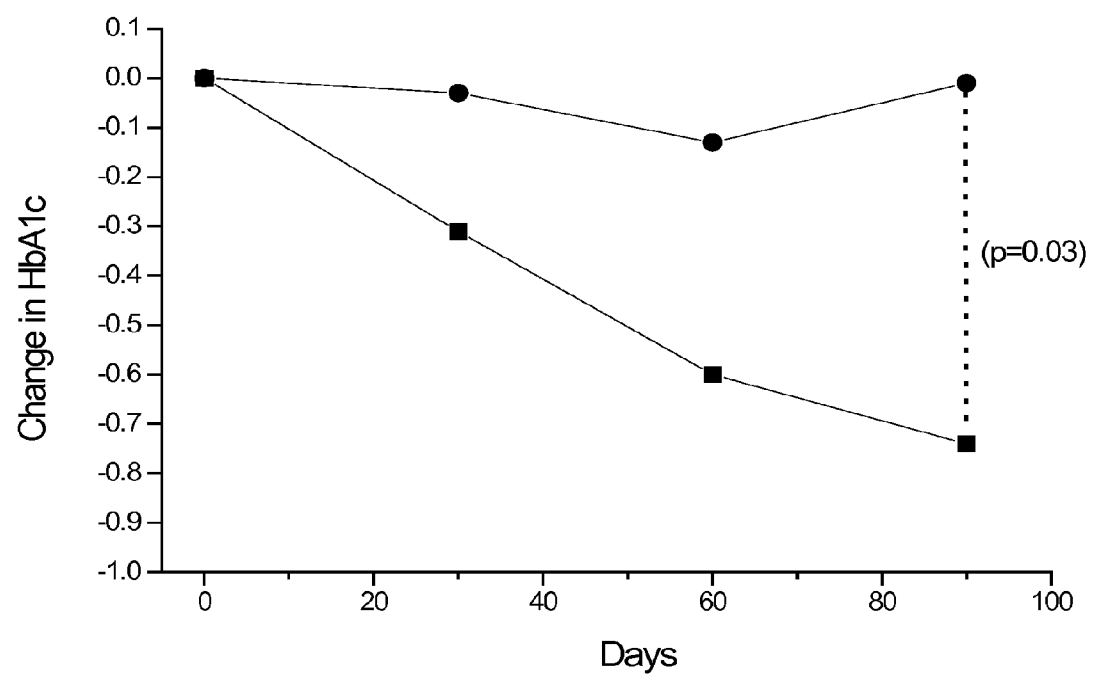
Figure 23:
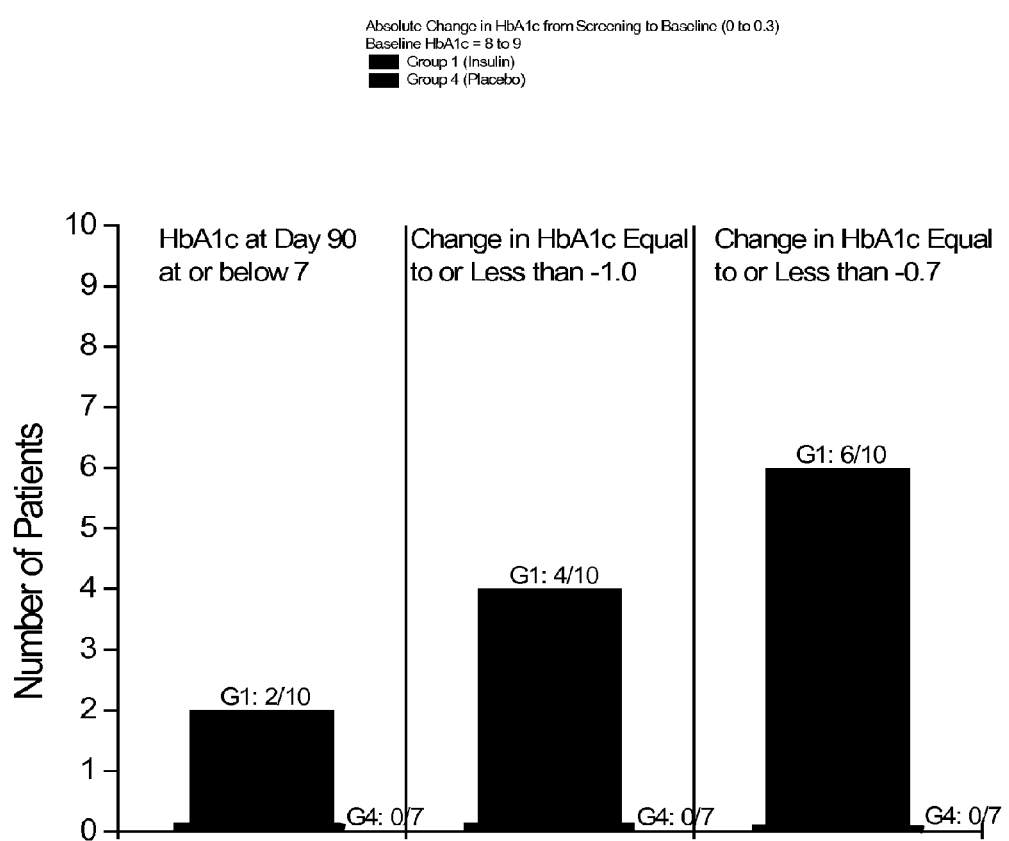
Figure 24:
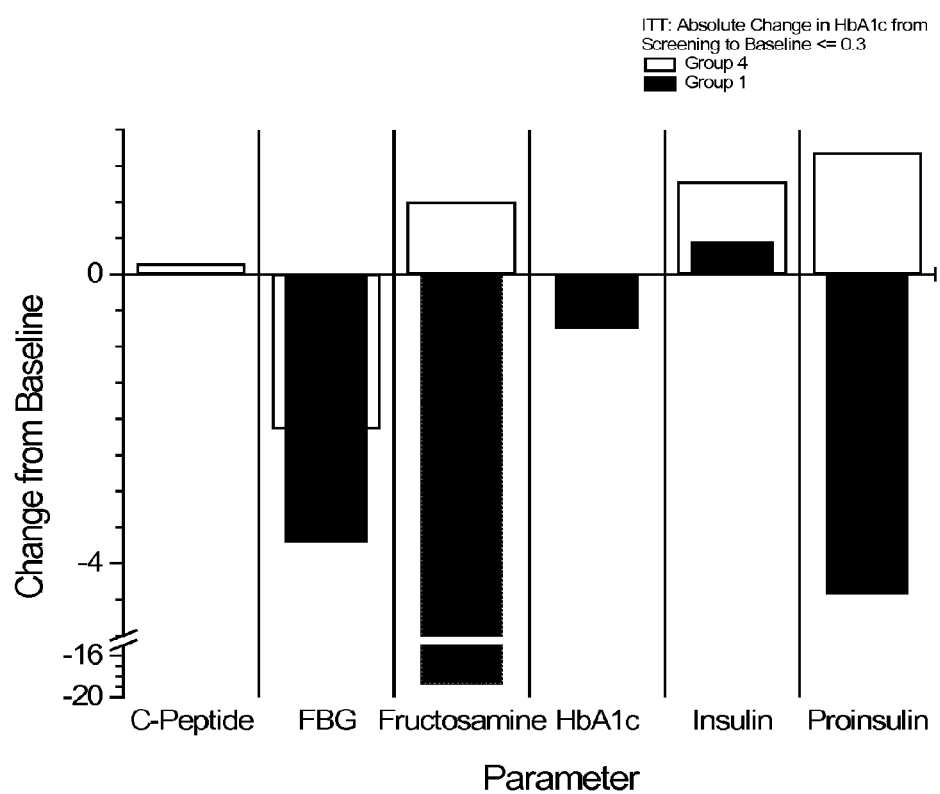

FIGS. 22-23 compare the changes in HbA1c levels for Groups 1 and 4 for those patients having a 0-0.3 variation of HbA1c levels between screening and at t=0, with baseline HbA1c levels between 8 and 8.9. For this population, FIG. 22 depicts changes in HbA1c levels across the 90 days for groups 1 and 4 and FIG. 23 depicts the number of patients reaching specified HbA1c target levels at the end of the study. FIG. 24 sets forth changes from baseline for C-Peptide, FBG, Fructosamine, HbA1c, Insulin and Proinsulin.

Amongst the participants in the study there were no significant adverse events, no episodes of severe hypoglycemia, or weight gain amongst groups I-III. Incidents of mild to moderate hypoglycemia and antibodies in groups 1-3 were comparable to those found in group 4 (placebo).

The invention claimed is:

1. A tablet consisting of 240 mg sodium 4-[(2-hydroxy-4-chlorobenzoyl)amino]butanoate, 12 mg gelatin, 5.45 mg insulin, 113.8 mg dibasic calcium phosphate and 3.75 mg magnesium stearate.

* * * * *